United States Patent [19]
Fisher

[11] Patent Number: 6,146,877
[45] Date of Patent: Nov. 14, 2000

[54] IDENTIFICATION OF THE PROGRESSION ELEVATED GENE-3 AND USES THEREOF

[75] Inventor: Paul B. Fisher, Scarsdale, N.Y.

[73] Assignee: The Trustees of Columbia University in the City of New York, New York, N.Y.

[21] Appl. No.: 08/821,818

[22] Filed: Mar. 21, 1997

[51] Int. Cl.[7] .............................. C07H 21/00; C12N 5/10; C12N 15/12; C12N 15/63

[52] U.S. Cl. .................................... 435/252.3; 435/254.2; 435/320.1; 435/325; 435/348; 435/419; 536/23.5; 536/25.1

[58] Field of Search .................................. 435/69.1, 91.1, 435/91.3, 252.3, 254.2, 320.1, 325, 348, 419; 514/44; 536/23.1, 23.5, 25.1; 935/4, 11, 66, 69, 70, 72

[56] References Cited

PUBLICATIONS

Report and Recommendations of the Panel to Assess the NIH Investment in Research on Gene Therapy, Orkin and Motulsky, co–chairs. National Institues of Health, Dec. 7, 1995.
Crystal. Transfer of genes to humans: Early lessons and obstacles to success. Science 270: 404–410, Oct. 1995.
Stull et al., Antigene, ribozyme and aptamer nucleic acid drugs: Progress and prospects. Pharm. Res. 12:465–483, Apr. 1995.
Babiss, P. B., et al. (1985) "Reversibility of Progression of the Transformed Phenotype in Ad5–Transformed Rat Embryo Cells," *Science* 228:1099–1101.
Fisher, P. B. (1984) in *Tumor Promotion and Cocarcinogenesis In Vitro, Mechanisms of Tumor Promotion*, ed. Slaga, T. J. (CRC Press, Boca Raton, FL), pp. 57–123.
Fisher, P. B., et al. (1979) "Tumor Promoters and Epidermal Growth Factor Stimulate Anchorage—Independent Growth of Adeovirus–Transformed Rat Embryo Cells," *Cell* 18:695–705.
Fisher, P. B., et al. (1979) "Tumour Promoters Enhance Anchorage—Independent Growth of Adenovirus–transformed Cells Without Altering the Integration Pattern of Viral Sequences," *Nature* 281:591–594.
Fisher, P. B., et al. (1979) "Phenotypic Properties and Tumor Promoter–induced Alterations in Rat Embryo Cells Transformed by Adenovirus," *Cancer Res.* 39:3051–3057.
He, B., et al. (1996) "The Carboxyl Terminus of the Murine MyD116 Gene Substitutes for the Corresponding Domain of the $\gamma_1$ 34.5 Gene of Herpes Simplex Virus To Preclude the Premature Shutoff of Total Protein Synthesis in Infected Human Cells," *J. Virol.* 70:84–90.
Jiang, H. and P. Fisher (1993) "Use of a Sensitive and Efficient Subtraction Hybridization Protocol for the Identification of Genes Differentially Regulated During the Induction of Differentiation in Human Melanoma Cells." *Mol Cell Different.* 1:285–299.
Reddy, P. G., et al. (1993) "Identification and Cloning of Genes Involved in Progression of Transformed Phenotype," in *Chromosome and Genetic Analysis, Methods in Molecular Genetics*, ed. Adolph, K. W. (Academic, Orlando FL), vol. 1, pp. 68–102.
Shen, R., et al. (1995) "Identification of the Human Prostatic Carcinoma Oncogene PTI–1 by Rapid Expression Cloning and Differential RNA Display," *PNAS USA* 92: 6778–6782.
Su, Z.-Z., et al. (1996) "Surface–epitope Masking and Expression Cloning Identifies the Human Prostate Carcinoma Tumor Antigen Gene PCTA–1 a Member of the Galectin Gene Family," *PNAS USA* 93:7252–7257.
Su, Z.-z., et al. (1993) "Defining the Critical Gene Expression Changes Associated with Expression and Suppression of the Tumorigenic and Metastic Phenotype in the Ha–ras–Transformed Cloned Rat Embryo Fibroblast Cells," *Oncogene* 8:1211–1219.
Su, Z.-z., et al. (1991) "Suppression of Adenovirus Type 5 E1A–Mediated Transformation and Expression of the Transformed Phenotype by Caffeic Acid Phenethyl Ester (CAPE)," *Mol. Carcinog* 4:231–242.
Su, Z-z., et al. (1991) "Induction of Transformation Progression in Type 5 Adenovirus–transformed Ray Embryo Cells by a Cloned Protein Kinase C $\beta_1$ Gene and Reversal of Progression by 5–azacytidine," *Oncogene* 9:1123–1132.
Zhan, Q., et al. (1994) The gadd and MyD Genes Define a Novel Set of Mammalian Genes Encoding Acidic Proteins That Synergistically Suppress Cell Growth, *Mol. Cell. Biol.* 14:2361–2371.

*Primary Examiner*—Remy Yucel
*Assistant Examiner*—Thomas G. Larson
*Attorney, Agent, or Firm*—John P. White; Cooper & Dunham LLP

[57] ABSTRACT

This invention provides an isolated nucleic acid molecule encoding a Progression Elevated Gene-3 protein. This invention also provides isolated nucleic acid molecule encoding a human Progression Elevated Gene-3 protein. This invention provides a nucleic acid molecule of at least 12 nucleotides capable of specifically recognizing a nucleic acid molecule encoding a Progression Elevated Gene-3 protein. This invention provides a method of detecting expression of the Progression Elevated Gene-3 in a sample. This invention provides an isolated nucleic acid molecule encoding a Progression Elevated Gene-3 protein operatively linked to a regulatory element. This invention provides a host vector system for the production of a polypeptide having the biological activity of a Progression Elevated Gene-3 protein. This invention also provides a purified Progression Elevated Gene-3 protein and a fragment thereof. This invention provides an antibody capable of specifically binding to a Progression Elevated Gene-3 protein. This invention provides a method for determining whether cells are in progression. This invention provides a method for diagnosing the aggressiveness of cancer cells by measuring the expression of Progression Elevated Gene-3. Finally, this invention provides various uses of the Progression Elevated Gene-3, its protein and the antibody against its protein.

15 Claims, 13 Drawing Sheets

FIGURE 3A

```
              1
PEG-3    MAPSPRPQHV LHMKEAHSFY LLSPLMGFLS RAWSRLRGPE VSEAMLAETV
GADD34   MAPSRPQHI  LWRDAHSFH  LLSPLMGFLS RAWSRLRVPE APEPWPAETV
MYD116   MAPSPRPQHV LHMRDAHNFY LLSPLMGLLS RAWSRLRGPE VPEAMLAKTV

51
PEG-3    AGANQIEADA LLTPPPVSEN HLPLRETEGN GTPEWSKAAQ RLCLDVEAQS
GADD34   TGADQIEADA HPAPPLVPEN HPPQGEAEES GTPEEGKAAQ GPCLDVQANS
MYD116   TGADQIEAAA LLTPTPVSGN LLPHGETEES GSPEQSQAAQ RLCLMEAES

101
PEG-3    SPPKTWGLSD IDEHNGKPGQ DGLREQEVEH GGPAEDEEDT HLQGADKKVG
GADD34   SPPETLGLSD DD....KQGQ DGPREQGRAH GCPSEEEEDG GLQSADKSLG
MYD116   SPPETWGLSN VDEYNAKPGQ DDLREKEMER GGPAENEEDG GLQGADKRLG

151
PEG-3    EVVAREEGVS ELAYPTSHWE ETVKKAHQAS .SGSHSRWE  AASIAPGYKP
GADD34   EVVAGEEGVT ELAYPTSHWE ETVKKAFRAS ADSI..PGHKS ADSI.PGHKS
MYD116   EVVAREEGVA EPAYPTSQLE ETV.KTYQAS SSGSHSRAWE AASIAPGYKP

201
PEG-3    STSVYCPGEA EHRATEEKGT DNKAEP..... ...VCSGSAF YHTRERPKQE
GADD34   STSVYCPGEA EHQATEEKQT ENKADPPSSP  SLSVSSGNAF YCS...KQE
MYD116   STPVPFLGEA EHQATEEKGT ENKADPSNSP  ..FVCTGNAF YYSREKPKQE

251
PEG-3    GETKPEQHRA GQSHPCQNAE AEEGGPETS. ..SGSHSRWE  LKAWVYRPGE
GADD34   GEADPEPHRA GKYQLCQNAE AEEEEAKVS  SGSHSRAWE  LKAWVYRPGE
MYD116   GEAKVEAHRA GQGHPCRNAE AEEGGPETT.               LKAWVYRPGE

301
PEG-3    DTEEEDSDL  DSAEEDT.AH TCTTPHTSAF LKAWVYRPGE DTEEED....
GADD34   DTEDDDSDW  GSAEEEGKAL SSPTSPEHDF LKAWVYRPGE DTEDDDDSDW
MYD116   DTEEEDNSDS DSAEEDT.AQ TGATPHTSAF LKAWVYRPGE DTEEEDSD..

```
              351                                                                         400
PEG-3         ..........  ..........  ..........  ..........  ..........  DSAEEDA.SQ
GADD34        GSAEEEGKAL  SSPTSPEHDF  ..........  LKAWVYRPGE  .....DGDW   GSAEKDGLAQ
MYD116        SDSAEEDTAG  TGATPHTSAF  ..........  LKAWVYRPGE  DTEDDQDSDW  DSAEEDT.AQ
              401                                                                         450
PEG-3         ..........  SCTTPHTSAF  LKAWVYRPGE  ..........  ..........  ..........
GADD34        ..........  TFATPHTSAF  LKTWVCCPGE  ..........  DT........  ..........
MYD116        ..........  TGATPHTSAF  LKAWVYRPGE  ..........  DTEEE.NSDL  ATPHTSPFLK
              451                                                                         500
PEG-3         ..........  ..........  ..........  ..........  ..........  ..........
GADD34        ..........  ..........  ..DTEEEDDS  DT........  ..........  ..........
MYD116        AWVYRPGEDT  EDDTEEEEDS  DTEEENSDLD  SAEEDTAQTG  SAEEDTAQTG  ..........
              501                                                                         550
PEG-3         ..........  ..........  ..........  ENVAPVDSET  VDSCQS....  TQHCLPVEKT
GADD34        KGCGEAEPPP  FQWPSIYL..  ..........  EVMVPEDSEA  ADPDKSPSHE  AQGCLPGEQT
MYD116        EGLVEAEHSL  FQ.VAFYLPG  ..........  ENVAPGDSET  ADSSQSPCLQ  PQRCLPGEKT
              551                                                                         600
PEG-3         KGRGE.EPPL  FQ.VAFYLPG  LRFL......  ...DRSQH    HLGLPLSCP.  ..FDCRSGSD
GADD34        LSKPPPGIRA  VHFSENVTVH  EKPAPPWTAP  KLPLRLQRRL  TLLRTPTQDQ
MYD116        DPETPLRARK  VHFAEKVTVH  EKPESPWAAP  KLPLRLQRRL  RLFKAPTRDQ
              601                                                                         650
PEG-3         ..........  ..........  FLAVWAGPAQ  AARRGPWEQL  ARDRSRFARR
GADD34        DPEIPLKARK  YLTPAFRARA  WARLGNPSLP  AARRGPWEQF  ARDRSRFARR
MYD116                    YLTPDSRARA  WARLRNPSLP  LALEPICDHT  FFPSQ.....
              651                                                                         669
PEG-3         ..........  ..........  ..........  QSEPRSSSEA  TPLTQDVTTP
GADD34        IAQAEEKLGP  ..........
MYD116        IAQAEEKLGP  SPLPSETPSP  SLYLGGRRG
```

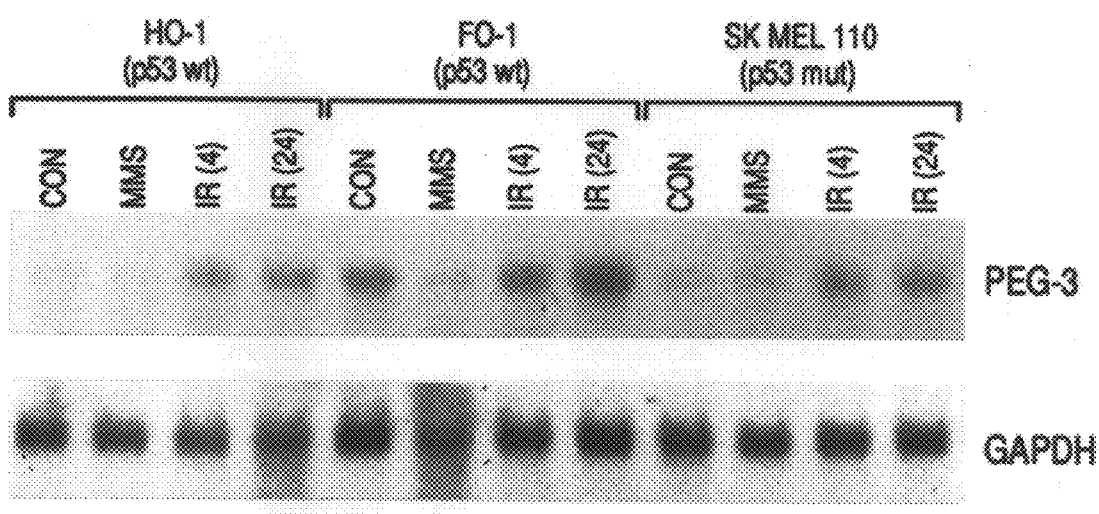

FIGURE 11

```
gtacttgtacattgctaaataaagagaggactccaggaggagcagcctgggtctaagag
gtaggcagaaggaggtttagggcctgagcacaagcttgaggagaaaggttattaaa
aagccagacgcttacagtgtgggctttggttctgagcagtctagcatgtgctgggttaaggaa
agggtttaagagtgtgggctttggttctgagcaatgctattaggaatttgaggcaggattcacgc
accaagtggcggagttgggttgtgagcaatgctattaggaatttgaggcaggattcacgc
gctgctgtgactattttaacaatgactcagtgctgtgacctgatactgtttccagagc
gacttctaaacaaattcccccttctaggccagacacacactcttctacctcctgtctccactgatgggctt
gcatgtcctgcactggaagaagccgcctgaggggcccgaggtctcagaggcctggttggcaga
cctcagccgggcctggagcgcctgagggggcccgaggtctcagaggcctggttggcaga
aacagtagcaggagcaaaccagatagaggctgaactcctgttgacgcctccccggtctc
tgaaatcacctactcctccgagagactggaagcccaaagttccctctaaaacttgggact
agcccagagctctgcctcgatgtgtggaagccaggacaagatggcctttagagagcaagaagt
ttcagatattgatgaacataatggagaagcaggacaagatggcctttagagagcaagaagt
ggagcacacagctggcctgcctactacagccctctcacctgcaagggcagataagaa
agttgggaggtgtgtgcagctgaggatgaagaagggtgtgtccgagctggcttacccacatcaca
ctggagaggtgtgtcagctgaggatgaagaaggatgtgtccgagctggcttacccacatcaca
ggcctctgctgcttccatagctccaggatataaaccagcactctgtgtattgcccagg
ggaggcagaacatcgagccacggagtaccacactagagagaacaataaggctgaaccctcagg
ctcccactccagagtctgggagtaccacactagagagaacctagcaggaggagaaac
taagccagagcaacacaggcaggcagagtcaccctttgtcagaatgcagagctgagga
aggaggacctgagacttctgtctgtctgcagtgccttcctgaaggctgggtgtatcg
cccagagaggacacagaggaggaagaagacagtgattggattcagctgaggaagacac
agctcatacctgtaccaccccatacaagtgcctttcctgaaggcctggtctatcgccc
aggagaggacacagaggaagatgacggtgattgggattcagctgaggaagacgcgtc
tcagagctgtaccacccccatacaagtgcctttcctgaaggcctggtctatcgcccagg
agaggacacagaggaagacgacagtgagaagttggcccagttgactcagaaacagt
tgactcttgccagagtaccccagcattgtctaccagtagagaagaccaaggatgtggaga
agcagagccccccctcccttccagtgcctcttactcgacgaagccagcaccacct
tgggctgccccctaaggccctgagattcctcgactgcaagccttcaaagcccc
gcccgaatcaggcccctgagattcctctgtctgggcaggaccagccaggctgctcgtcgaggccc
gttacagtccattttcttgctgtctgggcaggaccagccaggctgctcgtcgaggccc
tgggagcagttgcacgagatcgaagccgcttgctgcgacgcattgcctttctcctccactgcctgagccttgct
cttccactgagg
ccacacccccagccagccaagatgtgaccactccctccccttccagtgaaatccctcctc
cagcctgacttgggaggaaggcgggctaagcctgagtagtttttgtgtattctatga
gtgttagtctcttaatacgaatatgtaacgccttttgcatttgtaaaaaaaaaaaa
```

FIGURE 12

MAPSPRPQHV LHWKEAHSFY LLSPLMGFLS RAWSRLRGPE VSEAWLAETV
AGANQIEADA LLTPPPVSEN HLPLRETEGN GTPEWSKAAQ RLCLDVEAQS
SPPKTWGLSD IDEHNGKPGQ DGLREQEVEH TAGLPTLQPL HLQGADKKVG
EVVAREEGVS ELAYPTSHWE GGPAEDEEDT ETVKKAHQAS AASIAPGYKP
STSVYCPGEA EHRATEEKGT DNKAEPSGSH SRVWEYHTRE RPKQEGETKP
EQHRAGQSHP CQNAEAEEGG PETSVCSGSA FLKAWVYRPG EDTEEEEDSD
LDSAEEDTAH TCTTPHTSAF LKAWVYRPGE DTEEEDDGDW DSAEEDASQS
CTTPHTSAFL KAWVYRPGED TEEEDDSENV APVDSETVDS CQSTQHCLPV
EKTKGCGEAE PPPFQWPSIY LDRSQHHLGL PLSCPFDCRS GSDLSKPPPG
IRALRFL

IDENTIFICATION OF THE PROGRESSION ELEVATED GENE-3 AND USES THEREOF

The invention disclosed disclosed herein was made with United States Government support under National Institute of Health Grant CA 35675. Accordingly, the United States Government has certain rights in this invention.

BACKGROUND OF THE INVENTION

Throughout this application, various references are referred to within parentheses. Disclosures of these publications in their entireties are hereby incorporated by reference into this application to more fully describe the state of the art to which this invention pertains. Full bibliographic citations for these references may be found at the end of this application, preceding the claims.

The carcinogenic process involves a series of sequential changes in the phenotype of a cell resulting in the acquisition of new properties or a further elaboration of transformation-associated traits by the evolving tumor cell (1–4). Although extensively studied, the precise genetic mechanisms underlying tumor cell progression during the development of most human cancers remain enigmas. Possible factors contributing to transformation progression, include: activation of cellular genes that promote the cancer cell phenotype, i.e., oncogenes; activation or modification of genes that regulate genomic stability, i.e., DNA repair genes; loss or inactivation of cellular genes that function as inhibitors of the cancer cell phenotype, i.e. tumor suppressor genes; and/or combinations of these genetic changes in the same tumor cell (1–6). A useful model system for defining the genetic and biochemical changes mediating tumor progression is the type 5 adenovirus (Ad5)/early passage rat embryo (RE) cell culture system (1,7–14). Transformation of secondary RE cells by Ad5 is often a sequential process resulting in the acquisition of and further elaboration of specific phenotypes by the transformed cell (7–10). Progression in the Ad5-transformation model is characterized by the development of enhanced anchorage-independence and tumorigenic potential (as indicated by a reduced latency time for tumor formation in nude mice) by progressed cells (1,10). The progression phenotype in Ad5-transformed RE cells can be induced by selection for growth in agar or tumor formation in nude mice (7–10), referred to as spontaneous-progression, by transfection with oncogenes (13), such as Ha-ras, v-src, v-raf or the E6/E7 region of human papillomavirus type (HPV)-18, referred to as oncogene-mediated progression, or by transfection with specific signal transducing genes (14), such as protein kinase C, referred to as growth factor-related, gene-induced progression.

Progression, induced spontaneously or after gene transfer, is a stable cellular trait that remains undiminished in Ad5-transformed RE cells even after extensive passage (>100) in monolayer culture (13). However, a single-treatment with the demethylating agent 5-azacytidine (AZA) results in a stable reversion in transformation progression in >95% of cellular clones (10,13,14). The progression phenotype is also suppressed in somatic cell hybrids formed between normal or unprogressed transformed cells and progressed cells (11–13). These findings suggest that progression may result from the activation of specific progression-promoting genes or the selective inhibition of progression-suppressing genes, or possibly a combination of both processes.

The final stage in tumor progression is acquisition by transformed cells of the ability to invade local tissue, survive in the circulation and recolonize in a new area of the body, i.e., metastasis (15–17). Transfection of a *Ha-ras oncogene* into cloned rat embryo fibroblast (CREF) cells (18) results in morphological transformation, anchorage-independence and acquisition of tumorigenic and metastatic potential (19–21). Ha-ras-transformed CREF cells exhibit major changes in the transcription and steady-state levels of genes involved in suppression and induction of oncogenesis (21, 22). Simultaneous overexpression of the Ha-ras suppressor gene Krev-1 in Ha-ras-transformed CREF cells results in morphological reversion, suppression of agar growth capacity and a delay in in vivo oncogenesis (21). Reversion of transformation in Ha-ras+Krev-1 transformed CREF cells correlates with a return in the transcriptional and steady-state mRNA profile to that of untransformed CREF cells (21,22). Following long latency times, Ha-ras+Krev-1 transformed CREF cells form both tumors and metastases in athymic nude mice (21). The patterns of gene expression changes observed during progression, progression suppression and escape from progression suppression supports the concept of "transcriptional switching" as a major component of Ha-ras-induced transformation (21,22).

To identify potential progression inducing genes with elevated expression in progressed versus unprogressed Ad5-transformed cells we used subtraction hybridization (13,23). This approach resulted in the cloning of PEG-3 that is expressed at elevated levels in progressed cells (spontaneous, oncogene-induced and growth factor-related, gene-induced) than in unprogressed cells (parental Ad5-transformed, AZA-suppressed, and suppressed hybrids). Transfection of PEG-3 into unprogressed parental Ad5-transformed cells induces the progression phenotype, without significantly altering colony formation in monolayer culture or affecting cell growth. PEG-3 expression is also elevated following DNA damage and oncogenic transformation of CREF cells by various oncogenes. Sequence analysis indicates that PEG-3 has 73 and 68% nucleotide (nt) and 59 and 72% amino acid (aa) similarities, respectively, with the gadd34 and MyD116 gene. However, unlike gadd34 and MyD116 that encode proteins of ~65 and ~72 kDa, respectively, PEG-3 encodes a protein of ~50 kDa with only ~28 and ~40% aa similarities to gadd34 and MyD116, respectively, in its carboxyl terminus. These results indicate that PEG-3 represents a new member of the gadd34/MyD116 gene family with both similar and distinct properties. Unlike gadd34 and MyD116, which dramatically suppress colony formation (24), PEG-3 only modestly alters colony formation following transfection, i.e., ≦20% reduction in colony formation in comparison with vector transfected cells. Moreover, a direct correlation only exists between expression of PEG-3, and not gadd34 or Myd116, and the progression phenotype in transformed rodent cells. These findings provide evidence for a potential link between constitutive induction of a stress response, characteristic of DNA damage, and induction of cancer progression.

SUMMARY OF THE INVENTION

This invention provides an isolated nucleic acid molecule encoding a Progression Elevated Gene-3 protein. This invention also provides isolated nucleic acid molecule encoding a human Progression Elevated Gene-3 protein.

This invention provides a nucleic acid molecule of at least 12 nucleotides capable of specifically recognizing a nucleic acid molecule encoding a Progression Elevated Gene-3 protein. In a preferred embodiment, this nucleic acid molecule has a unique sequence of the Progression Elevated Gene-3.

This invention provides a method of detecting expression of the Progression Elevated Gene-3 in a sample which contains cells comprising steps of: (a) obtaining RNA from the cells; (b) contacting the RNA so obtained with a labelled probe of the Progression Elevated Gene-3 under hybridizing conditions permitting specific hybridization of the probe and the RNA; and (c) determining the presence of RNA hybridized to the molecule, thereby detecting the expression of the Progression Elevated Gene-3 in the sample.

This invention provides an isolated nucleic acid molecule encoding a Progression Elevated Gene-3 protein operatively linked to a regulatory element. This invention provides a host vector system for the production of a polypeptide having the biological activity of a Progression Elevated Gene-3 protein which comprises the vector having the sequence of Progression Elevated Gene-3 and a suitable host. This invention further provides a host vector system for the production of a polypeptide having the biological activity of the Progression Elevated Gene-3 protein.

This invention also provides a purified Progression Elevated Gene-3 protein and a fragment thereof. This invention also provides a polypeptide encoded by the isolated vertebrate nucleic acid molecule having a sequence of a Progression Elevated Gene-3.

This invention provides an antibody capable of specifically binding to a Progression Elevated Gene-3 protein.

This invention provides a method of transforming cells which comprises transfecting a host cell with a suitable vector having the sequence of a Progression Elevated Gene-3. This invention also provides the transformed cells produced by this method.

This invention provides a method for determining whether cells are in progression comprising steps of: a) measuring the expression of the Progression Elevated Gene-3; and b) comparing the expression measured in step a) with the expression of Progression Elevated Gene-3 in cells which are known not to be in progression, wherein an increase of the expression indicates that the cells are in progression.

This invention provides a method for determining whether a cancer cell is in a progression stage comprising measuring the expression of Progression Elevated Gene-3 in the cancer cell, wherein an increase in the amount indicates that the cancer cell is in progression.

This invention provides a method for diagnosing the aggressiveness of cancer cells comprising measuring the expression of Progression Elevated Gene-3 in the cancer cell, wherein an increase in the amount of the expression indicates that the cancer cell is more aggressive.

This invention provides a pharmaceutical composition for reversing the progression state of cells comprising an amount of the nucleic acid molecule capable of specifically hybridizing the Progression Elevated Gene-3 protein effective to inhibit the expression of Progression Elevated Gene-3 and a pharmaceutically acceptable carrier.

This invention provides a pharmaceutical composition for reversing the progression state of cells comprising an amount of the antibody or a functional fragment thereof which is capable of specifically recognizing the Progression Elevated Gene-3 protein effective to neutralize the action of the Progression Elevated Gene-3 protein and a pharmaceutically acceptable carrier.

This invention provides a method for producing cells which are resistant to progression comprising inhibiting or eliminating the expression of Progression Elevated Gene-3 in the cells. This invention also provides cells resulting from the method.

This invention provides a method for protecting cells from chemotherapeutic damage comprising inhibiting or eliminating the expression of Progression Elevated Gene-3 in the cells.

This invention provides a transgenic nonhuman living organism expressing Progression Elevated Gene-3 protein. In an embodiment, the living organism is animal.

This invention provides a cell having an exogenous indicator gene under the control of the regulatory element of a Progression Elevated Gene-3. In an embodiment, the cell is at progression. This cell may be produced by introducing an indicator gene to an E11-NMT, CREF-ras or CREF-src cell.

In a separate embodiment, the cell having an exogenous indicator gene under the control of the regulatory element of a Progression Elevated Gene-3 is not at progression. This cell may be produced by introducing an indicator gene to the E11 or the CREF cell.

This invention provides a method for determining whether an agent is capable of inhibiting DNA damage and repair pathways, cancer progression or oncogene mediated transformation comprising contacting an amount of the agent with the cell having an exogenous indicator gene under the control of the regulatory element of a Progression Elevated Gene-3, wherein a decrease of expression of the indicator gene indicates that the agent is capable of inhibiting DNA damage and repair pathways, cancer progression or oncogene mediated transformation.

This invention provides a method for determining whether an agent is capable of inducing DNA damage and repair pathways, cancer progression or oncogene mediated transformation comprising contacting an amount of the agent with the cell having an exogenous indicator gene under the control of the regulatory element of a Progression Elevated Gene-3 is not at progression, wherein an increase of expression of the indicator gene after the contact indicates that the agent is capable of inducing DNA damage and repair pathways, cancer progression or oncogene mediated transformation.

This invention provides a nucleic acid molecule comprising a sequence of the promoter of a Progression Elevated Gene-3 protein.

This invention also provides a nucleic acid molecule comprising Cis-Acting Regulatory Elements of the promoter of a Progression Elevated Gene-3 protein.

This invention also provides a Trans-Acting Regulatory Element that activates the expression of Progression Elevated Gene-3.

This invention further provides Trans-Acting Regulatory Element that suppresses the expression of Progression Elevated Gene-3.

This invention also provide an isolated nucleic acid molecule comprising sequence encoding the Trans-Acting Regulatory Element.

BRIEF DESCRIPTION OF THE FIGURES

FIGS. 3A and 3B. Predicted amino acid sequences of the PEG-3, gadd34 and MyD116 proteins. Sequences shared by the three genes are shaded. PEG-3 encodes a putative protein of 457 aa (MW of ~50 kDa) (SEQ ID NO:1), the gadd34 gene encodes a putative protein of 589 aa (MW ~65 kDa) (SEQ ID NO:2) and the MyD116 gene encodes a putative protein of 657 aa (MW of ~72 kDa) (SEQ ID NO:3).

FIG. 10 Effect of treatment with DNA damaging agents on PEG-3 expression in human melanoma cells. The indicated cell type was exposed to methyl methanesulfonate (MMS) (100 µg/ml for 2 hr and then grown in medium lacking MMS for 2 hr) or gamma irradiation (IR) (10Gy and cells were grown for 4 or 24 hr in medium) prior to RNA isolation. Fifteen µg of cellular RNA isolated from the indicated cell types and conditions, were electrophoresed, transferred to nylon membranes and hybridized with an ~700 bp 3' region of the PEG-3 gene (top) and then stripped and probed with GAPDH (bottom). HO-1 and F0-1 cells express wild-type p53 protein (p53 wt) and SK MEL 110 expresses a mutant p53 (p53 mut).

FIG. 11. Nucleotide sequence of Progression Elevated Gene-3 (PEG-3). The initiation and termination codons are underlined (SEQ ID NO:4).

FIG. 12 Amino acid sequence of Progression Elevated Gene-3 (PEG-3). PEG-3 protein contains 457 amino acids and with M.W. of approximately 50 kDa (SEQ ID NO:5).

DETAILED DESCRIPTION OF THE INVENTION

Figure 1:
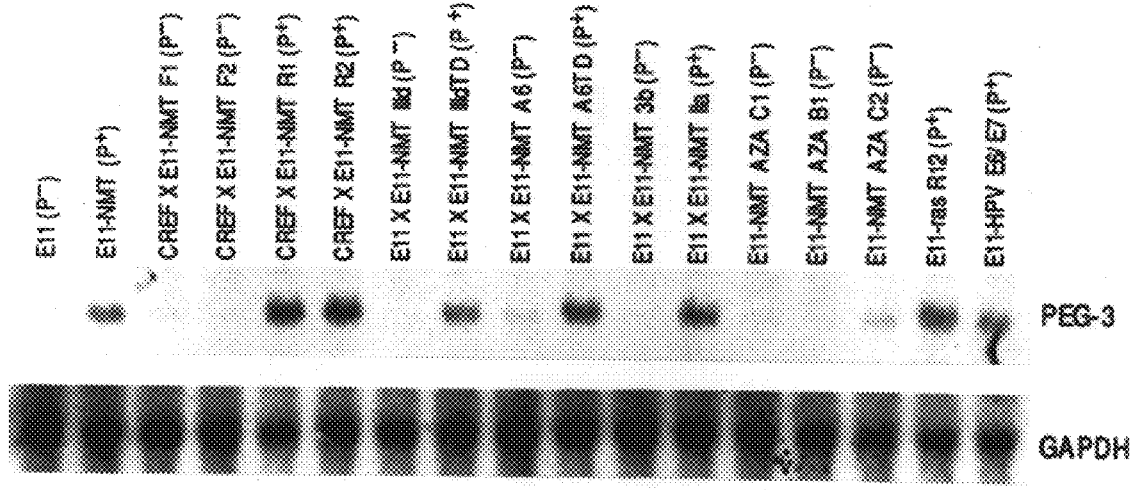
FIG. 1. PEG-3 expression in Ad5-transformed RE cells displaying different stages of transformation progression. Fifteen μg of cellular RNA isolated from the indicated cell types, were electrophoresed, transferred to nylon membranes and hybridized with an ~700 bp 3' region of the PEG-3 gene (top) and then stripped and probed with GAPDH (bottom).

This invention provides an isolated nucleic acid molecule encoding a Progression Elevated Gene-3 protein. The nucleic acid may be DNA, cDNA, genomic DNA or RNA.

This invention also encompasses DNAs and cDNAs which encode amino acid sequences which differ from those of Progression Elevated Gene-3 protein, but which should not produce phenotypic changes. Alternatively, this invention also encompasses DNAs and cDNAs which hybridize to the DNA and cDNA of the subject invention. Hybridization methods are well-known to those of skill in the art.

The DNA molecules of the subject invention also include DNA molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and additional analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

The DNA molecules described and claimed herein are useful for the information which they provide concerning the amino acid sequence of the polypeptide and as products for the large scale synthesis of the polypeptide by a variety of recombinant techniques. The molecule is useful for generating new cloning and expression vectors, transformed and transfected prokaryotic and eukaryotic host cells, and new and useful methods for cultured growth of such host cells capable of expression of the polypeptide and related products.

Moreover, the isolated nucleic acid molecules encoding a Progression Elevated Gene-3 are useful for the development of probes to study the progression of cancer.

This invention also provides isolated nucleic acid molecule encoding a human Progression Elevated Gene-3 protein.

This invention provides a nucleic acid molecule of at least 12 nucleotides capable of specifically recognizing a nucleic acid molecule encoding a Progression Elevated Gene-3 protein. In a preferred embodiment, this nucleic acid molecule has a unique sequence of the Progression Elevated Gene-3. The unique sequence of the Progression Elevated Gene-3 may easily be determined by comparing its sequence with known sequences which are available in different databases. The nucleic acid molecule may be DNA or RNA.

This nucleic acid molecule of at least 15 nucleotides capable of specifically hybridizing with a sequence of a nucleic acid molecule encoding a Progression Elevated Gene-3 protein can be used as a probe. Nucleic acid probe technology is well-known to those skilled in the art who will readily appreciate that such probes may vary greatly in length and may be labeled with a detectable label, such as a radioisotope or fluorescent dye, to facilitate detection of the probe. DNA probe molecules may be produced by insertion of a DNA molecule which encodes Progression Elevated Gene-3 protein into suitable vectors, such as plasmids or bacteriophages, followed by transforming into suitable bacterial host cells, replication in the transformed bacterial host cells and harvesting of the DNA probes, using methods well-known in the art. Alternatively, probes may be generated chemically from DNA synthesizers.

RNA probes may be generated by inserting the Progression Elevated Gene-3 molecule downstream of a bacteriophage promoter such as T3, T7 or SP6. Large amounts of RNA probe may be produced by incubating the labeled nucleotides with the linearized Progression Elevated Gene-3 fragment where it contains an upstream promoter in the presence of the appropriate RNA polymerase.

This invention provides a method of detecting expression of the Progression Elevated Gene-3 in a sample which contains cells comprising steps of: (a) obtaining RNA from the cells; (b) contacting the RNA so obtained with a labelled probe of the Progression Elevated Gene-3 under hybridizing conditions permitting specific hybridization of the probe and the RNA; and (c) determining the presence of RNA hybridized to the molecule, thereby detecting the expression of the Progression Elevated Gene-3 in the sample. mRNA from the cell may be isolated by many procedures well-known to a person of ordinary skill in the art. The hybridizing conditions of the labelled nucleic acid molecules may be determined by routine experimentation well-known in the art. The presence of mRNA hybridized to the probe may be determined by gel electrophoresis or other methods known in the art. By measuring the amount of the hybrid made, the expression of the Progression Elevated Gene-3 protein by the cell can be determined. The labelling may be radioactive. For an example, one or more radioactive nucleotides can be incorporated in the nucleic acid when it is made.

The RNA obtained in step (a) may be amplified by polymerase chain reaction (PCR) with appropriate primers. The appropriate primers may be selected from the known Progression Elevated Gene-3 sequences. Instead of detection by specific PEG-3 probe as described in the preceding paragraph, the specific amplified DNA by PCR is an indication that there is expression of Progression Elevated Gene-3.

This invention provides an isolated nucleic acid molecule encoding a Progression Elevated Gene-3 protein operatively linked to a regulatory element. In an embodiment, the vector is a plasmid.

This invention provides a host vector system for the production of a polypeptide having the biological activity of a Progression Elevated Gene-3 protein which comprises the vector having the sequence of Progression Elevated Gene-3 and a suitable host. The suitable host includes but is not limited to a bacterial cell, yeast cell, insect cell, or animal cell.

The isolated Progression Elevated Gene-3 sequence can be linked to different vector systems. Various vectors including plasmid vectors, cosmid vectors, bacteriophage vectors and other viruses are well-known to ordinary skilled practitioners. This invention further provides a vector which comprises the isolated nucleic acid molecule encoding for the Progression Elevated Gene-3 protein.

As an example to obtain these vectors, insert and vector DNA can both be exposed to a restriction enzyme to create complementary ends on both molecules which base pair with each other and are then ligated together with DNA ligase. Alternatively, linkers can be ligated to the insert DNA which correspond to a restriction site in the vector DNA, which is then digested with the restriction enzyme which cuts at that site. Other means are also available and known to an ordinary skilled practitioner.

In an embodiment, the rat PEG-3 sequence is cloned in the EcoRI site of pZeoSV vector. This plasmid, pPEG-3, was deposited on Mar. 5, 1997 with the American Type Culture Collection (ATCC), 10801 University Blvd. Manassas, Va., 20110-2209 U.S.A. under the provisions of the Budapest Treaty for the International Recognition of the Deposit of Microorganism for the Purposes of Patent Procedure. Plasmid, pPEG-3, was accorded ATCC Accession Number 97911.

This invention further provides a host vector system for the production of a polypeptide having the biological activity of the Progression Elevated Gene-3 protein. These vectors may be transformed into a suitable host cell to form a host cell vector system for the production of a polypeptide having the biological activity of the Progression Elevated Gene-3 protein.

Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well-known in the art, for example the methods described above for constructing vectors in general. Expression vectors are useful to produce cells that express the Progression Elevated Gene-3 protein.

This invention further provides an isolated DNA, cDNA or genomic DNA molecule described hereinabove wherein the host cell is selected from the group consisting of bacterial cells (such as *E.coli*), yeast cells, fungal cells, insect cells and animal cells. Suitable animal cells include, but are not limited to Vero cells, HeLa cells, Cos cells, CV1 cells and various primary mammalian cells.

This invention further provides a method of producing a polypeptide having the biological activity of the Progression Elevated Gene-3 protein which comprising growing host cells of a vector system containing Progression Elevated Gene-3 sequence under suitable conditions permitting production of the polypeptide and recovering the polypeptide so produced.

This invention provides a mammalian cell comprising a DNA molecule encoding a Progression Elevated Gene-3 protein, such as a mammalian cell comprising a plasmid adapted for expression in a mammalian cell, which comprises a DNA molecule encoding a Progression Elevated Gene-3 protein and the regulatory elements necessary for expression of the DNA in the mammalian cell so located relative to the DNA encoding the Progression Elevated Gene-3 protein as to permit expression thereof.

Various mammalian cells may be used as hosts, including, but not limited to, the mouse fibroblast cell NIH3T3, CHO cells, HeLa cells, Ltk⁻ cells, Cos cells, etc. Expression plasmids such as that described supra may be used to transfect mammalian cells by methods well-known in the art such as calcium phosphate precipitation, electroporation or DNA encoding the Progression Elevated Gene-3 protein may be otherwise introduced into mammalian cells, e.g., by microinjection, to obtain mammalian cells which comprise DNA, e.g., cDNA or a plasmid, encoding a Progression Elevated Gene-3 protein.

This invention also provides a purified Progression Elevated Gene-3 protein and a fragment thereof. As used herein, the term "purified Progression Elevated Gene-3 protein" shall mean isolated naturally-occurring Progression Elevated Gene-3 protein or protein manufactured such that the primary, secondary and tertiary conformation, and post-translational modifications are identical to naturally-occurring material as well as non-naturally occurring polypeptides having a primary structural conformation (i.e. continuous sequence of amino acid residues). Such polypeptides include derivatives and analogs. The fragment should bear biological activity similar to the full-length Progression Elevated Gene-3 protein.

This invention also provides a polypeptide encoded by the isolated vertebrate nucleic acid molecule having a sequence of a Progression Elevated Gene-3.

This invention provides an antibody capable of specifically binding to a Progression Elevated Gene-3 protein. The antibody may be polyclonal or monoclonal.

This invention provides a method to select specific regions on the Progression Elevated Gene-3 to generate antibodies. The protein sequence may be determined from the DNA sequence. The hydrophobic or hydrophilic regions in the protein will be identified. Usually, the hydrophilic regions will be more immunogenic than the hydrophobic regions. Therefore the hydrophilic amino acid sequences may be selected and used to generate antibodies specific to the Progression Elevated Gene-3 protein.

Polyclonal antibodies against these peptides may be produced by immunizing animals using the selected peptides. Monoclonal antibodies are prepared using hybridoma technology by fusing antibody producing B cells from immunized animals with myeloma cells and selecting the resulting hybridoma cell line producing the desired antibody. Alternatively, monoclonal antibodies may be produced by in vitro techniques known to a person of ordinary skill in the art. Specific antibody which only recognizes the Progression Elevated Gene-3 protein will then be selected. The selected antibody is useful to detect the expression of the Progression Elevated Gene-3 in living animals, in humans, or in biological tissues or fluids isolated from animals or humans.

This invention provides a method of transforming cells which comprises transfecting a host cell with a suitable vector having the sequence of a Progression Elevated Gene-3. This invention also provides the transformed cells produced by this method.

This invention provides a method for determining whether cells are in progression comprising steps of: a) measuring the expression of the Progression Elevated Gene-3; and b) comparing the expression measured in step a) with the expression of Progression Elevated Gene-3 in cells which are known not to be in progression, wherein an increase of the expression indicates that the cells are in progression. In an embodiment, the expression of Progression Elevated Gene-3 is measured by the amount of Progression Elevated Gene-3 mRNA expressed in the cells. In another embodiment, the expression of Progression Elevated Gene-3 is measured by the amount of the Progression Elevated Gene-3 protein expressed in the cells.

This invention provides a method for determining whether a cancer cell is in a progression stage comprising measuring the expression of Progression Elevated Gene-3 in the cancer cell, wherein an increase in the amount indicates that the cancer cell is in progression.

This invention provides a method for diagnosing the aggressiveness of cancer cells comprising measuring the expression of Progression Elevated Gene-3 in the cancer cell, wherein an increase in the amount of the expression indicates that the cancer cell is more aggressive.

This invention provides a pharmaceutical composition for reversing the progression state of cells comprising an amount of the nucleic acid molecule capable of specifically hybridizing the Progression Elevated Gene-3 protein effective to inhibit the expression of Progression Elevated Gene-3 and a pharmaceutically acceptable carrier.

Pharmaceutically acceptable carriers are well-known to those skilled in the art. Such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

This invention provides a pharmaceutical composition for reversing the progression state of cells comprising an amount of the antibody or a functional fragment thereof which is capable of specifically recognizing the Progression Elevated Gene-3 protein effective to neutralize the action of the Progression Elevated Gene-3 protein and a pharmaceutically acceptable carrier.

This invention provides a method for producing cells which are resistant to progression comprising inhibiting or eliminating the expression of Progression Elevated Gene-3 in the cells. This invention also provides cells resulting from the method.

This invention provides a method for protecting cells from therapeutic damage comprising inhibiting or eliminating the expression of Progression Elevated Gene-3 in the cells. In an embodiment, the damage is resulted from chemotherapy. In another embodiment, the damage is resulted from physical agent. Such physical agent includes but is not limited to gamma-irradiation.

One method to inhibit the expression of Progression Elevated Gene-3 is by expression of effective amount antisense RNA in the cell thereby inhibiting the expression of Progression Elevated Gene-3. The expression of Progression Elevated Gene-3 may be eliminated by deletion of the gene or introduction of mutation(s) to the gene.

This invention provides a transgenic nonhuman living organism expressing Progression Elevated Gene-3 protein. In an embodiment, the living organism is animal.

One means available for producing a transgenic animal, with a mouse as an example, is as follows: Female mice are mated, and the resulting fertilized eggs are dissected out of their oviducts. The eggs are stored in an appropriate medium. DNA or cDNA encoding a Progression Elevated Gene-3 is purified from a vector by methods well-known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

This invention provides a cell having an exogenous indicator gene under the control of the regulatory element of a Progression Elevated Gene-3. In an embodiment, the cell is at progression. This cell may be produced by introducing an indicator gene to an E11-NMT, CREF-ras or CREF-src cell.

In a separate embodiment, the cell having an exogenous indicator gene under the control of the regulatory element of a Progression Elevated Gene-3 is not at progression. This cell may be produced by introducing an indicator gene to the E11 or the CREF cell.

The indicator gene codes for beta-galactosidase, luciferase, chloramphenicol transferase or secreted alkaline phosphatase. Other indicator gene such as the Green Fluorescent Protein gene may be similar used in this invention. The indicator provides an easily detectable signal when the PEG-3 is expressed.

This invention provides a method for determining whether an agent is capable of inhibiting DNA damage and repair pathways, cancer progression or oncogene mediated transformation comprising contacting an amount of the agent with the cell having an exogenous indicator gene under the control of the regulatory element of a Progression Elevated Gene-3, wherein a decrease of expression of the indicator gene indicates that the agent is capable of inhibiting DNA damage and repair pathways, cancer progression or oncogene mediated transformation.

This invention provides a method for determining whether an agent is capable of inducing DNA damage and repair pathways, cancer progression or oncogene mediated transformation comprising contacting an amount of the agent with the cell having an exogenous indicator gene under the control of the regulatory element of a Progression Elevated Gene-3 is not at progression, wherein an increase of expression of the indicator gene after the contact indicates that the agent is capable of inducing DNA damage and repair pathways, cancer progression or oncogene mediated transformation.

Large scale of agents may be screened by the above two methods through automation. Indicator gene which produces color reaction may be selected.

This invention provides a cell having an exogenous suicidal gene or genes under the control of the regulatory element of a Progression Elevated Gene-3. Such "suicidal gene" will disrupt the normal progress of the cell. Preferably, the switching on of the suicidal gene will lead to cell death or halt in cell growth. Example of such genes are genes which lead to apotosis.

This invention provides a nucleic acid molecule comprising a sequence of the promoter of a Progression Elevated Gene-3 protein.

This invention also provides a nucleic acid molecule comprising Cis-Acting Regulatory Elements of the promoter of a Progression Elevated Gene-3 protein.

This invention also provides a Trans-Acting Regulatory Element that activates the expression of Progression Elevated Gene-3.

This invention further provides Trans-Acting Regulatory Element that suppresses the expression of Progression Elevated Gene-3.

This invention also provide an isolated nucleic acid molecule comprising sequence encoding the Trans-Acting Regulatory Element.

This invention will be better understood by reference to the Experimental Details which follow, but those skilled in the art will readily appreciate that the specific experiments detailed are only illustrative of the invention as described more fully in the claims which follow thereafter.

Experimental Details

Cancer is a progressive multigenic disorder characterized by defined changes in the transformed phenotype that culminates in metastatic disease. Determining the molecular basis of progression should lead to new opportunities for improved diagnostic and therapeutic modalities. Through the use of subtraction hybridization, a gene associated with transformation progression in virus and oncogene transformed rat embryo cells, progression elevated gene-3 (PEG-3), has been cloned. PEG-3 shares significant nucleotide and amino acid sequence homology with the hamster growth arrest and DNA damage inducible gene gadd34 and a homologous murine gene, MyD116, that is induced during induction of terminal differentiation by interleukin-6 in murine myeloid leukemia cells. PEG-3 expression is elevated in rodent cells displaying a progressed transformed phenotype and in rodent cells transformed by various oncogenes, including Ha-ras, v-src, mutant type 5 adenovirus (Ad5) and human papilloma virus-18. The PEG-3 gene is transcriptionally activated in rodent cells, as is gadd34 and MyD116, after treatment with DNA damaging agents, including methyl methanesulfonate and gamma irradiation. In contrast, only PEG-3 is transcriptionally active in rodent cells displaying a progressed phenotype. Although transfection of PEG-3 into normal and Ad5-transformed cells only marginally suppresses colony formation, stable overexpression of PEG-3 in Ad5-transformed rat embryo cells elicits the progression phenotype. These results indicate that PEG-3 is a new member of the gadd and MyD gene family with similar yet distinct properties and this gene may directly contribute to the transformation progression phenotype. Moreover, these studies support the hypothesis that constitutive expression of a DNA damage response may mediate cancer progression.

First Series of Experiments

Materials and Methods

Cell Lines, Culture Conditions and Anchorage-Independent Growth Assays. The isolation, properties and growth conditions of the E11, E11-NMT, E11-NMT X CREF somatic cell hybrids, E11 X E11-NMT somatic cell hybrids and the E11-NMT AZA clones have been described (1,7–13). E11-ras R12 and E11-HPV E6/E7 clones were isolated by transfection with the Ha-ras or the HPV-18 E6/E7 genes, respectively. The isolation, properties and growth conditions of CREF, CREF-H5hr1 A2, CREF-ras, the CREF-ras/Krev1 B1, B1 T and B1 M and the CREF-ras/Krev1 B2, B2 T, and B2 M clones have been described (21). CREF-src and CREF-HPV 18 clones were isolated by transfection with the v-src and HPV-18 E6/E7 genes, respectively. All cells were grown in Dulbecco's modified Eagle's minimum essential medium supplemented with 5% fetal bovine serum at 37° C. in a 5% $CO_2$ plus 95% air humidified incubator. Anchorage independence assays were performed by seeding various cell densities in 0.4% Noble agar on a 0.8% agar base layer both of which contain growth medium (7).

Cloning and Sequencing of the PEG-3 cDNA. The PEG-3 gene was cloned from E11-NMT cells using subtraction hybridization as described (23). A full-length PEG-3 cDNA was obtained using the rapid amplification of cDNA end (RACE) procedure and direct ligation (25,26). Sequencing was performed by the dideoxy-chain termination (Sanger) method (27). The coding region of PEG-3 was cloned into a pZeoSV vector (Invitrogen) as described (25,26).

RNA Analysis and In Vitro Transcription Assays. Total cellular RNA was isolated by the guanidinium/phenol extraction method and Northern blotting was performed as described (28). Fifteen μg of RNA were denatured with glyoxal/DMSO and electrophoresed in 1% agarose gels, transferred to nylon membranes and hybridized sequentially with $^{32}$P-labeled PEG-3, Ad5 E1A and GAPDH probes (28,29). Following hybridization, the filters were washed and exposed for autoradiography. The transcription rates of PEG-3, gadd34, MyD116, GAPDH and pBR322 was determined by nuclear run-on assays (12,21).

In Vitro Translation of PEG-3. Plasmid, pZeoSV, containing PEG-3 cDNA was linearized by digestion with Xho I and used as a template to synthesize mRNA. In vitro translation of PEG-3 mRNA was performed with a rabbit relticulocyte lysate translation kit as described by Promega.

DNA Transfection Assays. To study the effect of PEG-3 on monolayer colony formation the vector (pZeoSV) containing no insert or a pZeoSV-PEG-3 construct containing the PEG-3 coding region were transfected into the various cell types by the lipofectin method (GIBCO/BRL) and Zeocin resistant clones were isolated or efficiency of Zeocin colony formation was determined (29,30).

Results and Discussion

Expression of the PEG-3 Gene Correlates Directly with the Progression Phenotype in Viral and Oncogene Transformed Rodent Cells. A critical component of cancer development is progression, a process by which a tumor cell develops either qualitatively new properties or displays an increase in the expression of traits that enhance the aggressiveness of a tumor (1–4). Insight into this process offers the potential of providing important new targets for intervening in the neoplastic process (1–4). In the Ad5 transformed RE cell culture model system, enhanced anchorage-independent growth and in vivo tumorigenic aggressiveness, i.e., markers of the progression phenotype, are stable traits that can be induced spontaneously or by gene transfer (oncogenes and growth factor-related genes) (Table 1).

TABLE 1

Expression of PEG-3 in Ad5-transformed RE cells directly correlates with expression of the progression phenotype

| Cell Type[a] | Agar Cloning Efficiency (%)[b] | Tumorigenicity in Nude Mice[c] | Progression Phenotype[d] |
|---|---|---|---|
| RE | <0.001 | 0/10 | Prog⁻ |
| CREF | <0.001 | 0/18 | Prog⁻ |
| E11 | 2.9 ± 0.3 | 8/8(36) | Prog⁻ |
| E11-NMT | 34.3 ± 4.1 | 6/6(20) | Prog⁺ |
| CREF X E11-NMT F1 | 2.0 ± 0.3 | 0/6 | Prog⁻ |
| CREF X E11-NMT F2 | 1.5 ± 0.1 | 0/6 | Prog⁻ |
| CREF X E11-NMT R1 | 72.5 ± 9.4 | 3/3(17) | Prog⁺ |
| CREF X E11-NMT R2 | 57.4 ± 6.9 | 3/3(17) | Prog⁺ |
| E11 X E11-NMT IIId | 5.6 ± 0.7 | 3/3(56) | Prog⁻ |
| E11 X E11-NMT IIIdTD | 41.0 ± 4.9 | 3/3(19) | Prog⁺ |
| E11 X E11-NMT A6 | 0.3 ± 0.0 | 3/3(44) | Prog⁻ |
| E11 X E11-NMT A6TD | 29.3 ± 3.5 | N.T. | Prog⁺ |
| E11 X E11-NMT 3b | 1.5 ± 0.2 | 3/3(31) | Prog⁻ |
| E11 X E11-NMT IIA | 29.5 ± 2.8 | 3/3(23) | Prog⁺ |
| E11-NMT AZA C1 | 2.8 ± 0.5 | N.T. | Prog⁻ |
| E11-NMT AZA B1 | 1.6 ± 0.3 | 3/3(41) | Prog⁻ |
| E11-NMT AZA C2 | 2.0 ± 0.1 | 3/3(50) | Prog⁻ |
| E11-ras R12 | 36.8 ± 4.6 | 3/3(18) | Prog⁺ |
| E11-HPV E6/E7 | 31.7 ± 3.1 | 3/3(22) | Prog⁺ |

[a]Cell line descriptions can be found in Materials and Methods.
[b]Anchorage-independent growth was determined by seeding variable numbers of cells in 0.4% agar on a 0.8% agar base layer. Results are the average number of colonies from 4 replicate plates ± S.D.
[c]Tumorigenicity was determined by injecting nude mice with 2 × 10⁶ or 1 × 10⁷ (RE, CREF and CREF X E11-NMT hybrids). Results are the number of animals with tumors per number of animals injected and the number in parentheses indicate average latency time in days, i.e., first appearance of a palpable tumor. N.T. = not tested.
[d]Prog⁻ = progression phenotype is not expressed; Prog⁺ = progression phenotype is expressed.

Upon treatment of progressed cells with AZA, the progression phenotype can be stably reversed (1,10). A reversion of progression also occurs following somatic cell hybridization of progressed cells with unprogressed Ad5-transformed cells or with normal CREF cells. A further selection of these unprogressed Ad5-transformed cells by injection into nude mice results in acquisition of the progressed phenotype following tumor formation and establishment in cell culture. These studies document that progression in this model system is a reversible process that can be stably produced by appropriate cellular manipulation. In this context, the Ad5-transformed RE model represents an important experimental tool for identifying genes that are associated with and that mediate cancer progression.

To directly isolate genes elevated during progression we employed an efficient subtraction hybridization approach previously used to clone the p21 gene (melanoma differentiation associated gene-6; mda-6) (23,25) and a novel cancer growth suppressing gene mda-7 (26,29). For this approach, cDNA libraries from a progressed mutant Ad5 (H5ts125)-transformed RE clone, E11-NMT (10), and its parental unprogressed cells, E11 (10,31), were directionally cloned into the λ Uni-ZAP phage vector and subtraction hybridization was performed between double-stranded tester (E11-NMT) and single-stranded driver DNA (E11) by mass excision of the libraries (23). With this strategy in combination with the RACE procedure and DNA ligation techniques a full-length PEG-3 cDNA displaying elevated expression in E11-NMT versus E11 cells was cloned. Northern blotting analysis indicates that PEG-3 expression is ≧10-fold higher in all progressed Ad5-transformed RE cells, including E11-NMT, specific E11-NMT X CREF somatic cell hybrid clones, R1 and R2, expressing an aggressive transformed phenotype and specific E11 X E11-NMT somatic cell hybrid clones, such as IIa that display the progression phenotype (FIG. 1 and Table 1). PEG-3 mRNA levels also increase following induction of progression by stable expression of the Ha-ras and HPV-18 E6/E7 oncogenes in E11 cells (FIG. 1). A further correlation between expression of PEG-3 and the progression phenotype is provided by E11 X E11-NMT clones, such as IIId and A6, that initially display a suppression of the progression phenotype and low PEG-3 expression, but regain the progression phenotype and PEG-3 expression following tumor formation in nude mice, i.e., IIIdTD and A6TD (Table 1 and FIG. 1). In contrast, unprogressed Ad5-transformed cells, including E11 , E11-NMT X CREF clones F1 and F2, E11 X E11-NMT clones IIId, A6 and 3b and AZA-treated E11-NMT clones B1, C1 and C2, have low levels of PEG-3 RNA. These results provide evidence for a direct relationship between the progression phenotype and PEG-3 expression in this Ad5-transformed RE cell culture system. They also demonstrate that the final cellular phenotype, i.e., enhanced anchorage-independence and aggressive tumorigenic properties, is a more important determinant of PEG-3 expression than is the agent (oncogene) or circumstance (selection for tumor formation in nude mice) inducing progression.

Figure 2:
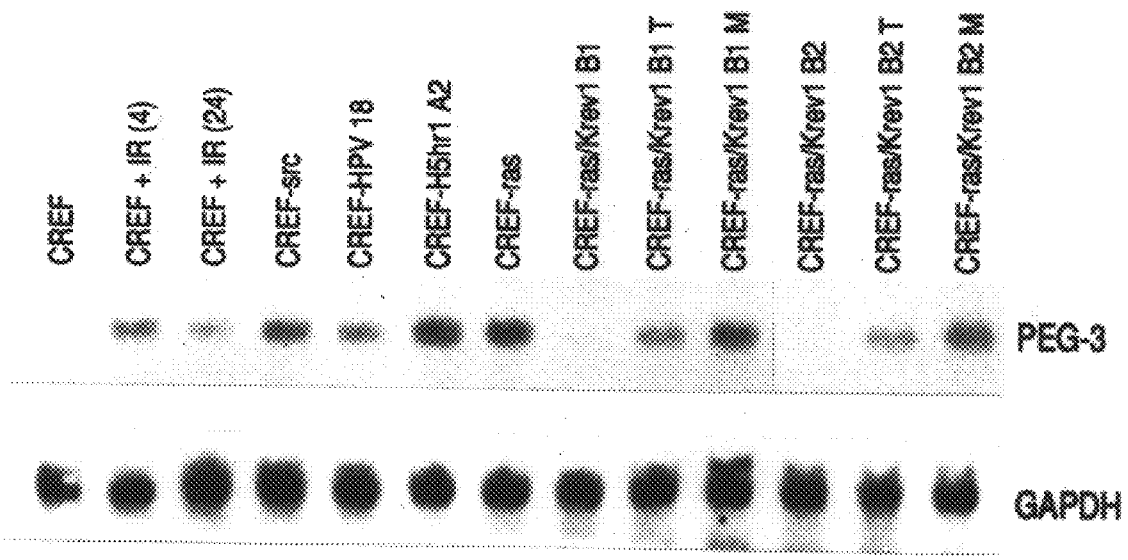
FIG. 2. PEG-3 expression in gamma irradiated and oncogene transformed CREF cells. The experimental procedure was as described in the legend to FIG. 1. CREF cells were gamma irradiated with 10 Gy and RNA was isolated 4 and 24 hr later. Fifteen µg of cellular RNA isolated from the indicated cell types, were electrophoresed, transferred to nylon membranes and hybridized with an ~700 bp 3' region of the PEG-3 gene (top) and then stripped and probed with GAPDH (bottom).

A second rodent model used to study the process of cancer progression employs CREF clones modified by transfection to express dominant acting oncogenes (such as Ha-ras, v-src, HPV-18 and the mutant adenovirus H5hrl) and tumor suppressor genes (such as Krev-1, RB and wild-type p53) (19–22 and unpublished data). In this model system, Ha-ras-transformed CREF cells are morphologically transformed, anchorage-independent and induce both tumors and lung metastases in syngeneic rats and athymic nude mice (19–22). The Krev-1 (Ha-ras) suppressor gene reverses the in vitro and in vivo properties in Ha-ras transformed cells (21). Although suppression is stable in vitro, Ha-ras/Krev-1 CREF cells induce both tumors and metastases after extended times in nude mice (21). Expression of PEG-3 is not apparent in CREF cells, whereas tumorigenic CREF cells transformed by v-src, HPV-18, H5hr1 and Ha-ras contain high levels of PEG-3 RNA (FIG. 2). Suppression of Ha-ras induced transformation by Krev-1 inhibits PEG-3 expression. However, when Ha-ras/Krev-1 cells escape tumor suppression and form tumors and metastases in nude mice, PEG-3 expression reappears, with higher expression in metastatic-derived than tumor-derived clones (FIG. 2). These findings provide further documentation of a direct relationship between induction of a progressed and oncogenic phenotype in rodent cells and PEG-3 expression. As indicated above, it is the phenotype rather than the inducing agent that appears to be the primary determinant of PEG-3 expression in rodent cells.

Figure 4:
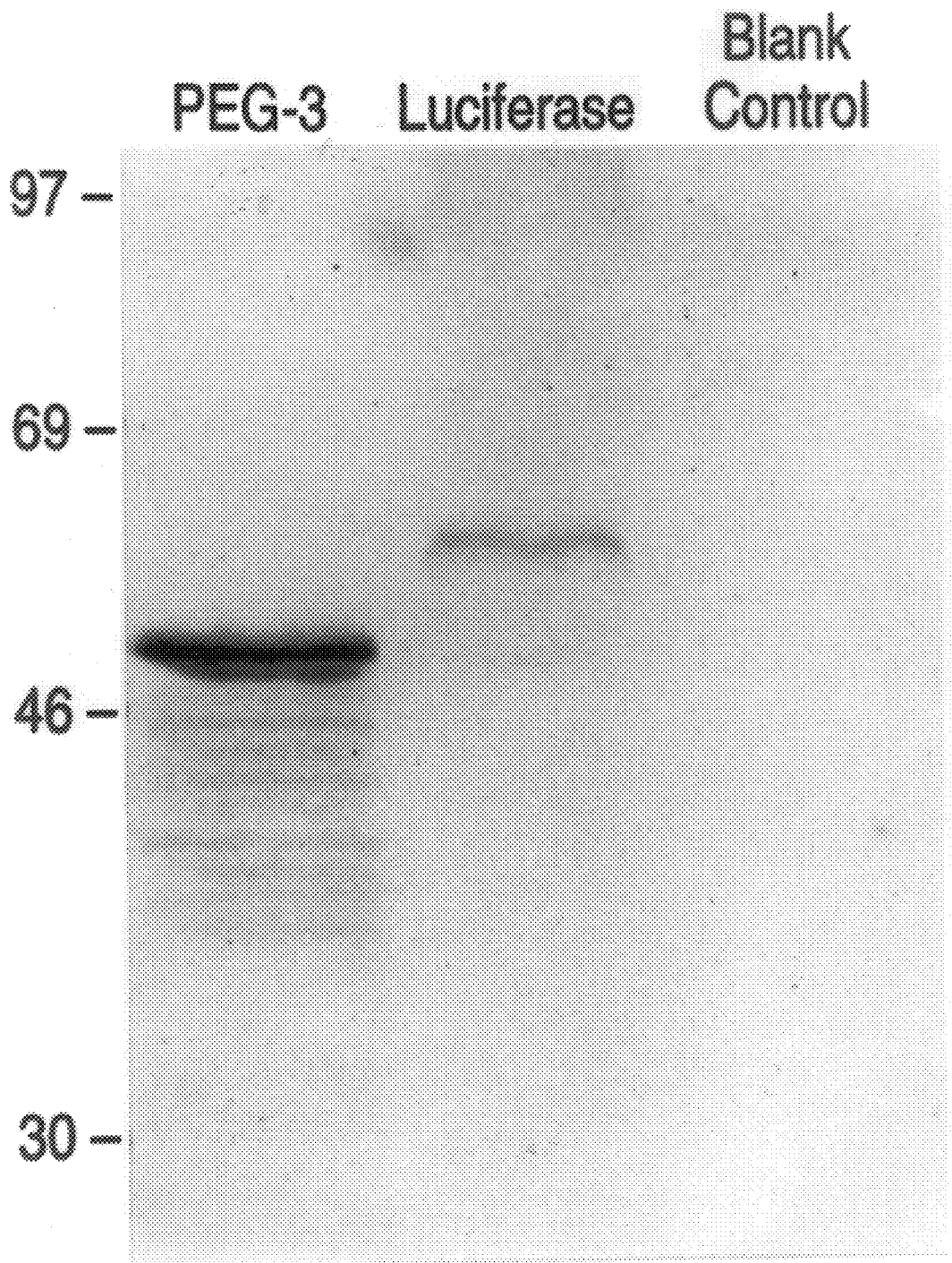
FIG. 4. In vitro translation of the PEG-3 gene. Lane Luciferase is the in vitro translation of the luciferase gene (~61 kDa), positive control. The blank lane contains the same reaction mixture without mRNA, negative control. Lane PEG-3 contains the translated products of this cDNA. Rainbow protein standards (Amersham) were used to determine the sizes of the in vitro translated products.

The PEG-3 Gene Displays Sequence Homology with the Hamster gadd34 and Mouse MyD116 Genes and is Inducible by DNA Damage. The cDNA sizes of PEG-3, gadd34 and MyD116 are 2210, 2088 and 2275 nt, respectively. The nt sequence of PEG-3 is ~73% and the aa sequence is ~59% homologous to the gadd34 (32) gene (FIG. 3 and data not shown). PEG-3 also shares significant sequence homology, ~68% nt and ~72% aa, with the murine homologue of gadd34, MyD116 (33,34) (FIG. 3 and data not shown). Differences are apparent in the structure of the 3' untranslated regions of PEG-3 versus gadd34/MyD116. ATTT motifs have been associated with mRNA destabilization. In this context, the presence of 3 ATTT sequences in Gadd34 and 6 tandem ATTT motifs in MyD116 would predict short half-lives for these messages. In contrast, PEG-3 contains only 1 ATTT motif suggesting that this mRNA may be more stable. The sequence homologies between PEG-3 and gadd34/MyD116 are highest in the amino terminal region of their encoded proteins, i.e., ~69 and ~76% homology with gadd34 and Myd116, respectively, in the first 279 aa. In contrast, the sequence of the carboxyl terminus of PEG-3 significantly diverges from gadd34/Myd116, i.e., only ~28 and ~40% homology in the carboxyl terminal 88 aa. In gadd34 and MyD116 a series of similar 39 aa are repeated in the protein, including 3.5 repeats in gadd34 and 4.5 repeats in MyD116. In contrast, PEG-3 contains only 1 of these 39 aa regions, with ~64% and ~85% homology to gadd34 and MyD116, respectively. On the basis of sequence analysis, the PEG-3 gene should encode a protein of 457 aa with a predicted MW of ~50 kDa. To confirm this prediction, in vitro translation analyses of proteins encoded by the PEG-3 cDNA were determined (FIG. 4). A predominant protein after in vitro translation of PEG-3 has a molecular mass of ~50 kDa (FIG. 4). In contrast, gadd34 encodes a predicted protein of 589 aa with an $M_W$ of ~65 kDa and MyD116 encodes a predicted protein of 657 aa with an $M_W$ of ~72 kDa. The profound similarity in the structure of PEG-3 versus gadd34/MyD116 cDNA and their encoded proteins suggest that PEG-3 is a new member of this gene family. Moreover, the alterations in the carboxyl terminus of PEG-3 may provide a functional basis for the different properties of this gene versus gadd34/MyD116.

Figure 5:
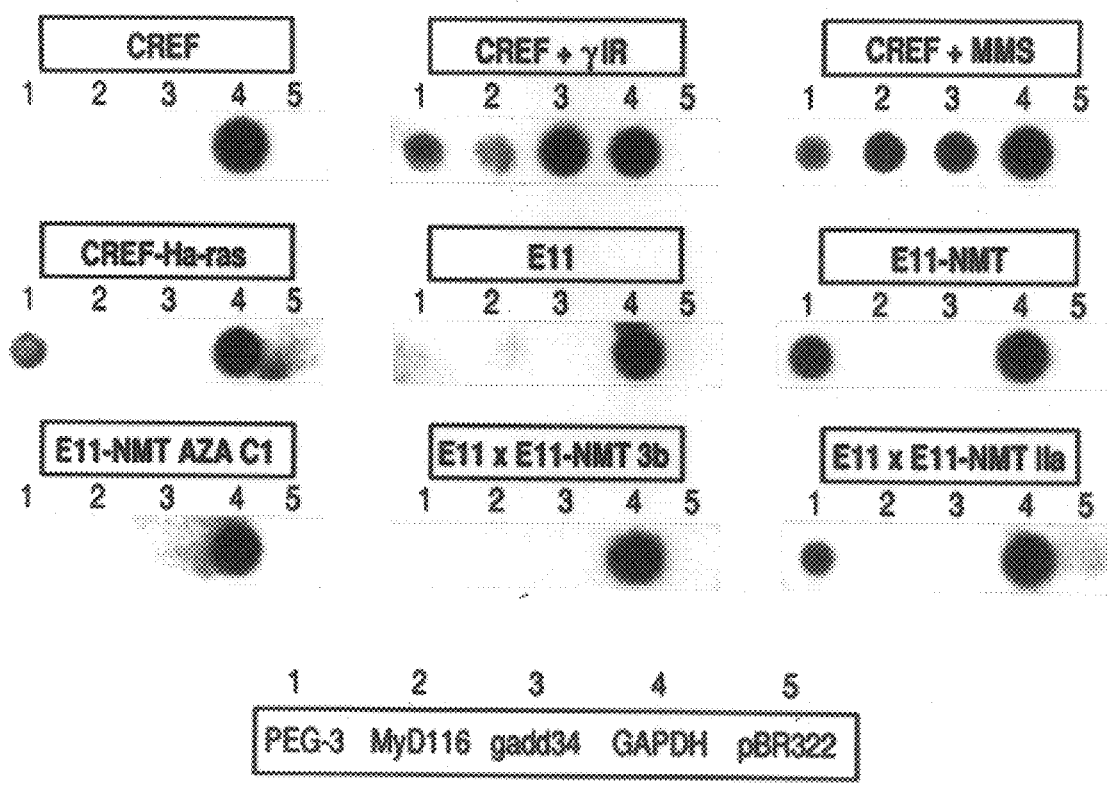
FIG. 5. Transcription of the PEG-3, gadd34 and MyD116 genes as a function of DNA damage and transformation progression. Nuclear run-on assays were performed to determine comparative rates of transcription. Nuclei were isolated from CREF cells treated with MMS (100 µg/ml for 2 hr followed by growth for 4 hr in complete medium) or gamma irradiation (10 Gy followed by 2 hr growth in complete medium). DNA probes include, PEG-3 (1), MyD116 (2), gadd34(3), GAPDH (4) and pBR322(5).

The specific role of the gadd34/MyD116 gene in cellular physiology is not known. Like hamster gadd34 and its murine homologue MyD116, PEG-3 steady-state mRNA and RNA transcriptional levels are increased following DNA damage by methyl methanesulfonate (MMS) and gamma irradiation (γIR) (FIGS. 2 and 5 and data not shown). In contrast, nuclear run-on assays indicate that only the PEG-3 gene is transcriptionally active (transcribed) as a function of transformation progression (FIG. 5). This is apparent in CREF cells transformed by Ha-ras and in E11-NMT and various E11-NMT subclones either expressing or not expressing the progression phenotype (FIG. 5). The gadd34/MyD116 gene, as well as the gadd45, MyD118 and gadd153 genes, encode acidic proteins with very similar and unusual charge characteristics (24). PEG-3 also encodes a putative protein with acidic properties similar to the gadd and MyD genes (FIG. 3). The carboxyl-terminal domain of the murine MyD116 protein is homologous to the corresponding domain of the herpes simplex virus 1 $\gamma_1 34.5$ protein, that prevents the premature shutoff of total protein synthesis in infected human cells (35,36). Replacement of the carboxyl-terminal domain of $\gamma_1 34.5$ with the homologous region from MyD116 results in a restoration of function to the herpes viral genome, i.e., prevention of early host shutoff of protein synthesis (36). Although further studies are required, preliminary results indicate that expression of a carboxyl terminus region of MyD116 results in nuclear localization (36). Similarly, gadd45, gadd153 and MyD118 gene products are nuclear proteins (24,37). Moreover, both gadd45 and MyD118 interact with the DNA replication and repair protein proliferating cell nuclear antigen (PCNA) and the cyclin-dependent kinase inhibitor p21 (37). MyD118 and gadd45 also modestly stimulate DNA repair in vitro (37). The carboxyl terminus of PEG-3 is significantly different than that of MyD116 (FIG. 3). Moreover, the carboxyl-terminal domain region of homology between MyD116 and the $\gamma_1 34.5$ protein is not present in PEG-3. In this context, the localization, protein interactions and properties of PEG-3 may be distinct from gadd and MyD genes. Once antibodies with the appropriate specificity are produced it will be possible to define PEG-3 location within cells and identify potentially important protein interactions mediating biological activity. This information will prove useful in elucidating the function of the PEG-3 gene in DNA damage response and cancer progression.

PEG-3 Lacks Potent Growth Suppressing Properties Characteristic of the gadd and Myd Genes. An attribute shared by the gadd and MyD genes is their ability to markedly suppress growth when expressed in human and murine cells (24,37). When transiently expressed in various human tumor cell lines, gadd34/MyD116 is growth inhibitory and this gene can synergize with gadd45 or gadd153 in suppressing cell growth (24). These results and those discussed above suggest that gadd34/MyD116, gadd45, gadd153 and MyD118, represent a novel class of mammalian genes encoding acidic proteins that are regulated during DNA damage and stress and involved in controlling cell growth (24,37). In this context, PEG-3 would appear to represent a paradox, since its expression is elevated in cells displaying an in vivo proliferative advantage and a progressed transformed and tumorigenic phenotype.

Figure 6:
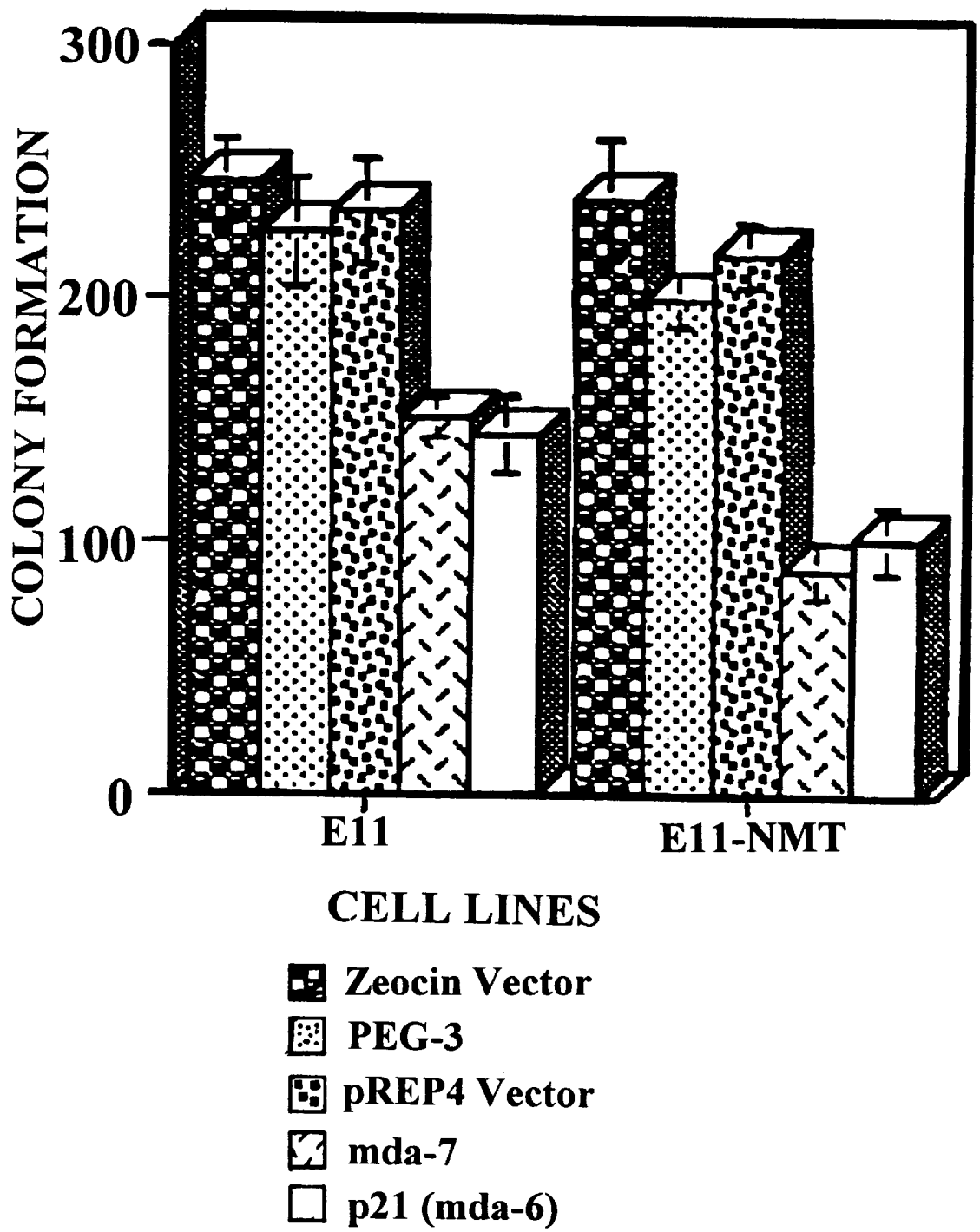
FIG. 6. Effect of transfection with PEG-3, mda-7 and p21 (mda-6) on colony formation of E11 and E11-NMT cells in monolayer culture. Target cells were transfected with 10 µg of a Zeocin vector (pZeoSV), the PEG-3 gene cloned in pZeoSV (PEG-3), the pREP4 vector, the mda-7 gene cloned in pREP4 (mda-7) and the mda-6 (p21) gene cloned in pREP4 (p21 (mda-6). Data represents the average number of Zeocin or hygromycin (pREP4 transfection) resistant colonies±S.D. for 4 plates seeded at $1 \times 10^5$ cells/6-cm plate.

To determine the effect of PEG-3 on growth, E11 and E11-NMT cells were transfected with the protein coding region of the PEG-3 gene cloned into a Zeocin expression vector, pZeoSV (FIG. 6). This construct permits an evaluation of growth in Zeocin in the presence and absence of PEG-3 expression. E11 and E11-NMT cells were also transfected with the p21 (mda-6) and mda-7 genes, previously shown to display growth inhibitory properties (25,26,29). Colony formation in both E11 and E11-NMT cells is suppressed 10 to 20%, whereas the relative colony formation following p21 (mda-6) and mda-7 transfection is decreased by 40 to 58% (FIG. 6 and data not shown). Colony formation is also reduced by 10 to 20% when PEG-3 is transfected into CREF, normal human breast (HBL-100) and human breast carcinoma (MCF-7 and T47D) cell lines (data not shown). Although the gadd and MyD genes were not tested for growth inhibition in E11 or E11-NMT cells, previous studies indicate colony formation reductions of >50 to 75% in several cell types transfected with gadd34, gadd45, gadd153, MyD116 or MyD118 (24,37). The lack of dramatic growth suppressing effects of PEG-3 and its direct association with the progression state suggest that this gene may represent a unique member of this acidic protein gene family that directly functions in regulating progression. This may occur by constitutively inducing signals that would normally only be generated during genomic stress. In this context, PEG-3 might function to alter genomic stability and facilitate tumor progression. This hypothesis is amenable to experimental confirmation.

Figure 7:
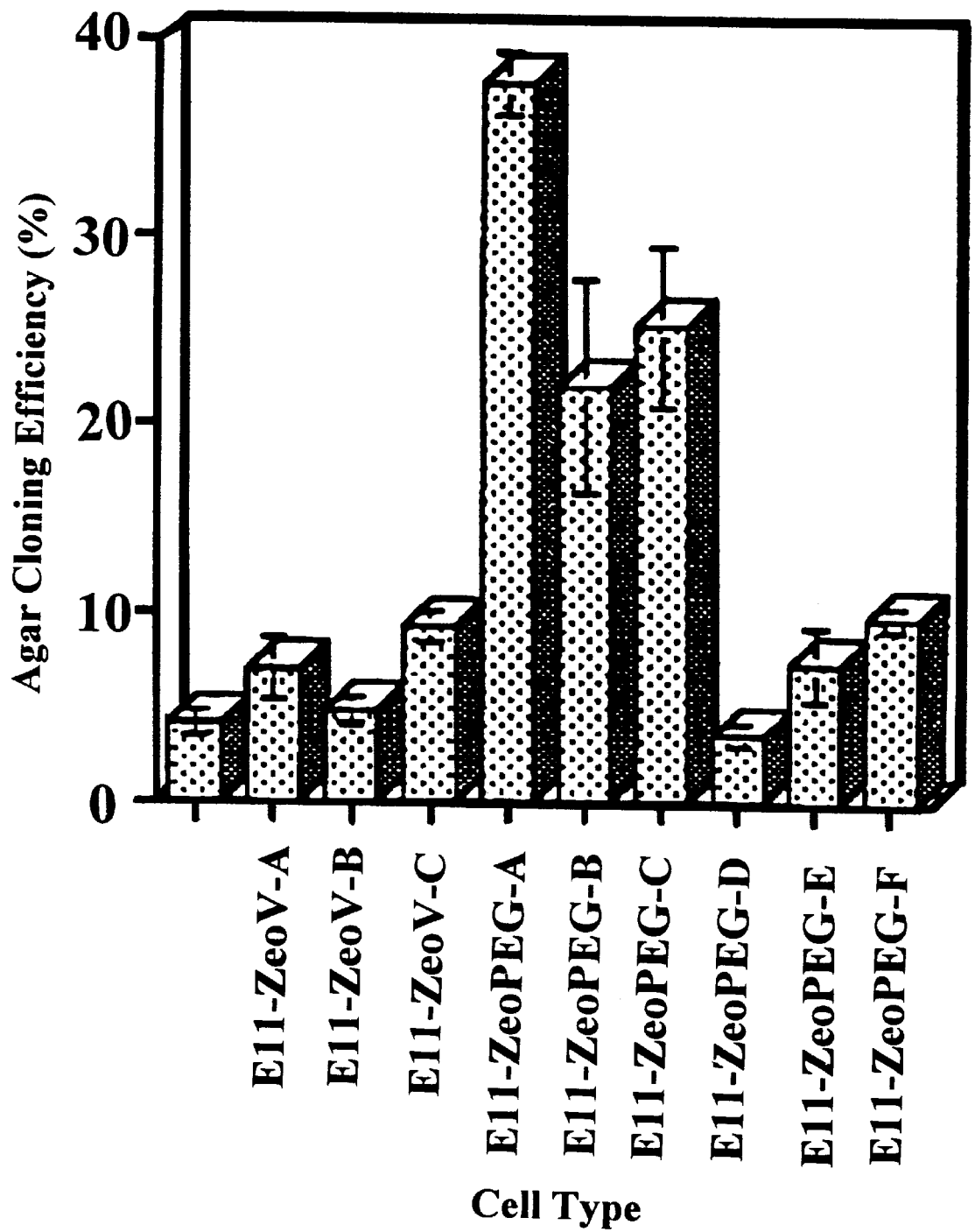
FIG. 7. Effect of stable PEG-3 expression on anchorage-independent growth of E11 cells. Agar cloning efficiency of E11, Zeocin resistant pZeoV (vector) transfected E11 and Zeocin resistant pZeoPEG transfected E11 cells. Average number of colonies developing in 4 replicate plates±S.D.
Figure 8:
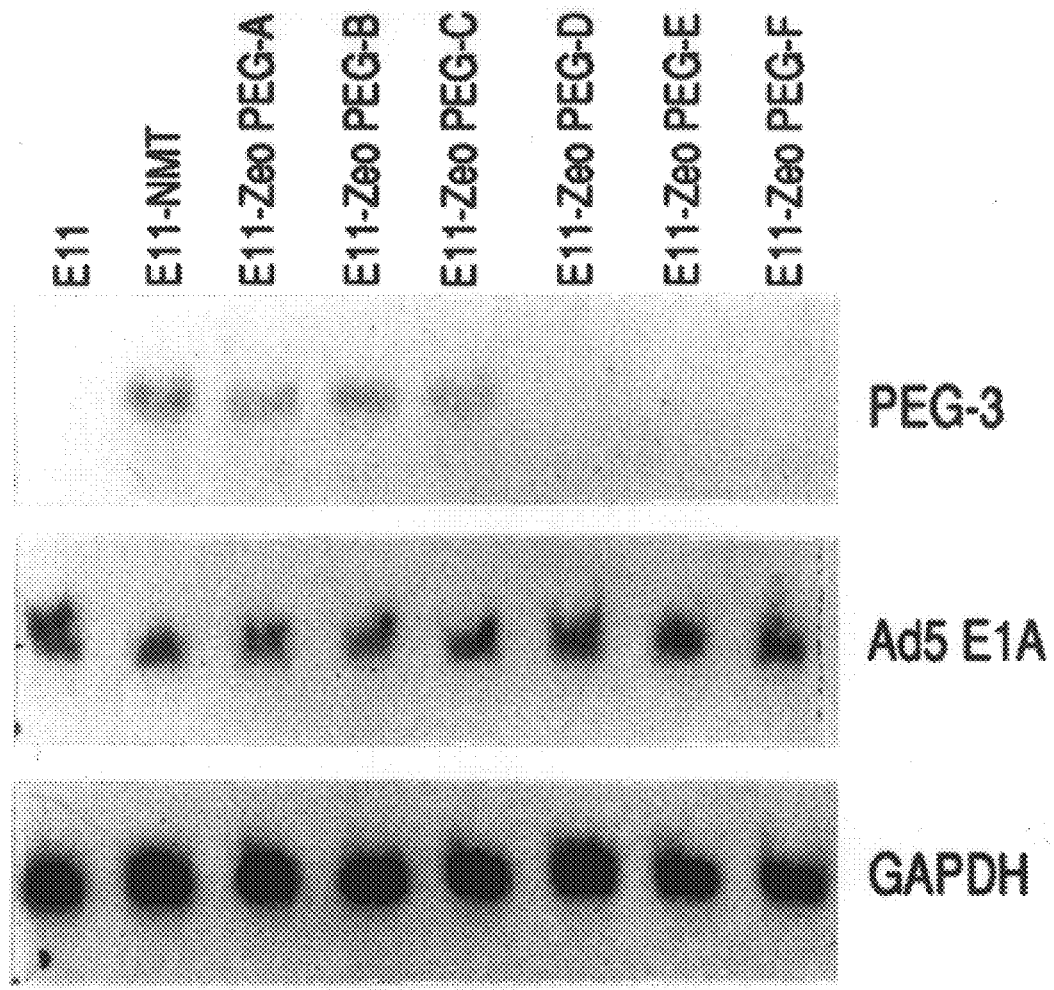
FIG. 8. Expression of PEG-3, Ad5 E1A and GAPDH RNA in pZeoPEG transfected E11 cells. The experimental procedure was as described in the legend to FIG. 1. Blots were probed sequentially with PEG-3 (top), Ad5 E1A (middle) and GAPDH (bottom). The E11-ZeoPEG clones are the same clones analyzed for anchorage-independence in FIG. 7.

PEG-3 Induces a Progression Phenotype in Ad5-Transformed RE Cells. An important question is whether PEG-3 expression simply correlates with transformation progression or whether it can directly contribute to this process. To distinguish between these two possibilities we have determined the effect of stable elevated expression of PEG-3 on expression of the progression phenotype in E11 cells. E11 cells were transfected with a Zeocin expression vector either containing or lacking the PEG-3 gene and random colonies were isolated and evaluated for anchorage independent growth (FIG. 7). A number of clones were identified that display a 5- to 9-fold increase in agar cloning efficiency in comparison with E11 and E11-Zeocin vector transformed clones. To confirm that this effect was indeed the result of elevated PEG-3 expression, independent Zeocin resistant E11 clones either expressing or not expressing the progression phenotype were analyzed for PEG-3 mRNA expression (FIG. 8). This analysis indicates that elevated anchorage-independence in the E11 clones correlates directly with increased PEG-3 expression. In contrast, no change in Ad5 E1A or GAPDH mRNA expression is detected in the different clones. These findings demonstrate that PEG-3 can directly induce a progression phenotype without altering expression of the Ad5 E1A transforming gene. Further studies are required to define the precise mechanism by which PEG-3 elicits this effect.

Cancer is a progressive disease characterized by the accumulation of genetic alterations in an evolving tumor (1–6). Recent studies provide compelling evidence that mutations in genes involved in maintaining genomic stability, including DNA repair, mismatch repair, DNA replication, microsattelite stability and chromosomal segregation, may mediate the development of a mutator phenotype by cancer cells, predisposing them to further mutations resulting in tumor progression (38). Identification and characterization of genes that can directly modify genomic stability and induce tumor progression will provide significant insights into cancer development and evolution. This information would be of particular benefit in defining potentially novel targets for intervening in the cancer process. Although the role of PEG-3 in promoting the cancer phenotype remains to be defined, the current studies suggest a potential causal link between constitutive induction of DNA damage response pathways, that may facilitate genomic instability, and cancer progression. In this context, constitutive expression of PEG-3 in progressing tumors may directly induce genomic instability or it may induce or amplify the expression of down-stream genes involved in this process. Further studies are clearly warranted and will help delineate the role of an important gene, PEG-3, in cancer.

Conclusion

Subtraction hybridization results in the identification and cloning of a gene PEG-3 with sequence homology and DNA damage inducible properties similar to gadd34 and MyD116. However, PEG-3 expression is uniquely elevated in all cases of rodent progression analyzed to date, including spontaneous and oncogene-mediated, and overexpression of PEG-3 can induce a progression phenotype in Ad5-transformed cells. Our studies suggest that PEG-3 may represent an important gene that is both associated with (diagnostic) and causally related to cancer progression. They also provide a potential link between constitutive expression of a DNA damage response pathway and progression of the transformed phenotype.

FIRST SERIES OF REFERENCES

1. Fisher, P. B. (1984) in *Tumor Promotion and Cocarcinogenesis In Vitro, Mechanisms of Tumor Promotion,* ed. Slaga, T. J. (CRC Press, Boca Raton, Fla.), pp. 57–123.
2. Bishop, J. M. (1991) *Cell* 64:235–248.
3. Vogelstein, B. & Kinzler, K. W. (1991) *Trends Genet.* 9:138–141.
4. Knudson, A. G. (1993) *Proc. Natl. Acad. Sci. USA* 90:10914–10921.
5. Levine, A. J. (1993) *Annu. Rev. Biochem.* 62:623–651.
6. Hartwell, L. H. & Kastan, M. B. (1994) *Science* 266:1821–1828.
7. Fisher, P. B., Goldstein, N. I. & Weinstein, I. B. (1979) *Cancer Res.* 39:3051–3057.
8. Fisher, P. B., Dorsch-Hasler, K., Weinstein, I. B. & Ginsberg, H. S. (1979) *Nature* 281:591–594.
9. Fisher, P. B., Bozzone, J. H. & Weinstein, I. B. (1979) *Cell* 18:695–705.

10. Babiss, P. B., Zimmer, S. G. & Fisher, P. B. (1985) *Science* 228:1099–1101.
11. Duigou, G. J., Babiss, L. E., Iman, D. S., Shay J. W. & Fisher, P. B. (1990) *Mol. Cell. Biol.* 10:2027–2034.
12. Duigou, G. J., Su, Z.-z., Babiss, L. E., Driscoll, B., Fung, Y.-K.T. & Fisher, P. B. (1991) *Oncogene* 6:1813–1824.
13. Reddy, P. G., Su, Z.-z. & Fisher, P. B. (1993) in *Chromosome and Genetic Analysis, Methods in Molecular Genetics,* ed. Adolph, K. W. (Academic, Orlando, Fla.), Vol. 1, pp. 68–102.
14. Su, Z.-z., Shen, R., O'Brian, C. A. & Fisher, P. B. (1994) *Oncogene* 9:1123–1132.
15. Fidler, I. J. (1990) *Cancer Res.* 50:6130–6138.
16. Liotta, L. A., Steeg, P. G. & Stetler-Stevenson, W. G. (1991) *Cell* 64:327–336.
17. Fidler, I. J. (1995) *J. Natl. Cancer Inst.* 87:1588–1592.
18. Fisher, P. B., Babiss, L. E., Weinstein, I. B. & Ginsberg, H. S. (1982) *Proc. Natl. Acad. Sci. USA* 79:3527–3531.
19. Boylon, J. F., Jackson, J., Steiner, M., Shih, T. Y., Duigou, G. J., Roszman, T., Fisher, P. B. & Zimmer, S. G. (1990) *Anticancer Res.* 10:717–724.
20. Boylon, J. F., Shih, T. Y., Fisher, P. B. & Zimmer, S. G. (1992) *Mol. Carcinog.* 3:309–318.
21. Su, Z.-z., Austin, V. N., Zimmer, S. G. & Fisher, P. B. (1993) *Oncogene* 8:309–318.
22. Su, Z.-z., Yemul, S., Estabrook, A., Friedman, R. M., Zimmer, S. G. & Fisher, P. B. (1995) *Intl. J. Oncology* 7:1279–1284.
23. Jiang, H. & Fisher, P. B. (1993) *Mol. Cell. Different.* 1:285–299.
24. Zhan, Q., Lord, K. A., Alamo, I., Jr., Hollander, M. C., Carrier, F., Ron, D., Kohn, K. W., Hoffman, B., Liebermann, D. A. & Fornace, A. J., Jr. (1994) *Mol. Cell. Biol.* 14:2361–2371.
25. Jiang, H., Lin, J., Su, Z.-z., Kerbel, R. S., Herlyn, M., Weissman, R. B., Welch, D. R. & Fisher, P. B. (1995) *Oncogene* 10:1855–1864.
26. Jiang, H., Lin, J. J., Su, Z.-z., Goldstein, N. I. & Fisher, P. B. (1995) *Oncogene* 11:2477–2486.
27. Su, Z.-z., Leon, J. A., Jiang, H., Austin, V. A., Zimmer, S. G. & Fisher, P. B. (1993) *Cancer Res.* 53:1929–1938.
28. Jiang, H., Su, Z.-z., Datta, S., Guarini, L., Waxman, S. & Fisher, P. B.(1992) *Intl. J. Oncol.* 1:227–239.
29. Jiang, H., Su, Z.-z., Lin, J. J., Goldstein, N. I., Young, C. S. H. & Fisher, P. B. (1996) *Proc. Natl. Acad. Sci. USA* 93:9160–9165.
30. Su, Z.-z., Grunberger, D. & Fisher, P. B. (1991). *Mol. Carcinog* 4:231–242.
31. Fisher, P. B., Weinstein, I. B., Eisenberg, D. & Ginsberg, H. S. (1978) *Proc. Natl. Acad. Sci. USA* 75:2311–2314.
32. Fornace, A. J., Jr., Alamo, I., Jr. & Hollander, M. C. (1988) *Proc. Natl. Acad. Sci. USA* 85:8800–8804.
33. Lord, K. A., Hoffman-Liebermann, B. & Liebermann, D. A. (1990) *Oncogene* 5:387–396.
34. Lord, K. A., Hoffman-Liebermann, B. & Liebermann, D. A. (1990) *Nucleic Acids Res.* 18:2823.
35. Chou, J. & Roizman, B. (1994) *Proc. Natl. Acad. Sci. USA* 91:5247–5251.
36. He, B., Chou, J., Liebermann, D. A., Hoffman, B. & Roizman, B. (1996) *J. Virol.* 70:84–90.
37. Vairapandi, M., Balliet, A. G., Fornace, A. J., Jr., Hoffman, B. & Liebermann, D. A. (1996) *Oncogene* 11:2579–2594.
38. Loeb, L. A. (1994) *Cancer Res.* 54:5059–5063.

Second Series of Experiments
Development of Biosensor Systems to Efficiently and Selectively Detect Agents Inducing and Inhibiting DNA Damage Pathways, Oncogenic Transformation and Cancer Progression The PEG-3 gene is induced in a p53-independent manner in E11, CREF and human melanoma cells following treatment with DNA damaging agents, such as gamma irradiation (1 and unpublished data). Nuclear run-on assays, that measure rates of gene transcription, indicate that induction of PEG-3 by DNA damage and expression of PEG-3 in cells displaying the progression phenotype (such as E11-NMT and CREF cells transformed by various oncogenes) involves elevated transcription of this gene (1). This data supports the hypothesis that the appropriate transcriptional regulating factors are inducible following DNA damage in cells and they are constitutively expressed in progressed cells. Since transcription of genes involves elements located in the promoter region of genes, current data supports the hypothesis that the promoter region of the PEG-3 gene is directly regulated as a function of genotoxic stress, oncogenic transformation and during cancer progression. This finding will be exploited by isolating the promoter of PEG-3 (as described below), linking this DNA sequence to a β-galactosidase (β-gal) reporter gene and constructing cells that either constitutively express this reporter gene (E11-NMT-β-gal, CREF-ras-β-gal and CREF-src-β-gal) cr cells that contain a DNA damage inducible reporter gene (E11-β-gal and CREF-β-gal). The E11-NMT-β-gal, CREF-ras-β-gal and CREF-src-β-gal constructs can be used as sensitive and selective monitors for agents that can inhibit DNA damage and repair pathways, cancer progression and oncogene mediated transformation. Conversely, the E11-β-gal and CREF-β-gal cell constructs can be used as sensitive and selective monitors for conditions and agents that induce DNA damage and repair pathways and may also induce the progression and oncogene-mediated transformed phenotypes. The ability to modify β-gal expression, as a function of activation or suppression of the PEG-3 promoter region or factors that interact with the promoter region, can easily be assessed using the appropriate substrate (5-bromo-4-chloro-3-indolyl-beta-D-galacto-pyranoside (X-gal) that is converted into a final product (5-bromo-4-chloro-3-indole) that has a blue color. E11-NMT-β-gal cells will normally stain blue following addition of the appropriate substrate. However, should expression from the PEG-3 promoter region be suppressed this will extinguish β-gal expression thereby resulting in a loss of blue staining following addition of the substrate. These rapid, efficient and selective biosensor systems can easily be formatted for the screening of an infinite number of compounds with potential cancer progression suppression, oncogene suppression and DNA damage inhibiting functions. E11-β-gal and CREF-β-gal cells will normally not stain blue following addition of the substrate. However, should the promoter region be activated, following induction of appropriate DNA damage and repair pathways or expression of specific oncogenes, the β-gal gene will be activated resulting in a blue stain following addition of the substrate. These rapid, efficient and selective biosensor systems can easily be formatted for the screening of an infinite number of compounds with potential cancer progression, oncogene transformation and DNA damage inducing properties. These model systems will prove valuable in identifying agents and elucidating pathways involved in cancer progression, oncogenic transformation and DNA damage induction and repair. This should lead to the development of novel therapeutics to prevent genomic damage and instability, thereby inhibiting cancer progression and oncogene mediated-transformation, and the identification of new classes of agents that can prevent DNA damage and enhance DNA damage repair.

1. Identification and Characterization of the Promoter Region of PEG-3, Cis-Acting Regulatory Elements of the PEG-3 Promoter and Trans-Acting Regulatory Elements that Activate (or Repress) PEG-3 Expression Overview Nuclear run-on studies indicate that the PEG-3 gene is constitutively transcribed in progressed E11-NMT, CREF cells treated with methyl methanesulfonate (MMS) or gamma irradiation and in CREF-cells transformed by various oncogenes, such as Ha-ras and v-src. Studies will, therefore, be conducted to (i) clone the 5'-flanking region of the PEG-3 gene and analyze its activity in E11 and E11-NMT, CREF and DNA damaged CREF and CREF cells transformed by various oncogenes; (ii) identify cis-acting regulatory elements in the promoter region of the PEG-3 gene which are responsible for the differential induction of expression in the different cell types and under different experimental conditions; and (iii) identify and characterize trans-acting regulatory elements which activate (or repress) expression of the PEG-3 gene.

To elucidate the mechanism underlying the transcriptional regulation of the PEG-3 gene the 5'-flanking region of this gene will be analyzed. This will be important for studies determining regulatory control of the PEG-3 gene including autoregulation, developmental regulation, tissue and cell type specific expression, DNA damage induction and differential expression in cells displaying a progressed cancer phenotype. The isolation of the promoter region will also be necessary for creating a biosensor model for monitoring and analyzing factors involved in mediating DNA damage and repair and oncogenic transformation and cancer progression. Once the appropriate sequence of the PEG-3 gene regulating the initiation of transcription has been identified, studies can be conducted to determine relevant trans-acting regulatory factors that bind to specific cis-acting regulatory elements and activate or repress the expression of the PEG-3 gene. These molecules may provide important clues for understanding the pathways governing DNA damage and repair mechanisms underlying cancer progression. Ultimately, such an understanding may uncover important targets for directly modifying and intervening in these phenotypes and processes.

Cloning the promoter region of the PEG-3 gene and testing its function. To identify the promoter region of PEG-3 we have used a human PromoterFinder™ DNA Walking Kit (Clontech) (2,3), This PCR-based method facilitates the cloning of unknown genomic DNA sequences adjacent to a known cDNA sequence. Using this approach an ~2 kb fragment of PEG-3 that may contain the promoter region of this gene has been isolated. The putative 5' flanking-region of PEG-3 has been subcloned into the pBluescript vector and sequenced by the Sanger dideoxynucleotide procedure. To verify the transcriptional start site deduced from the cDNA, primer extension analysis will be performed (4). In case of the identification of multiple putative ATG or start sites RNase protection assays will be performed using oligonucleotides spanning the 5' end of the PEG-3 cDNA sequence (4,5). To define the boundary of the PEG-3 promoter region, a heterologous expression system containing a bacterial chloramphenicol acetyltransferase (CAT) or luciferase gene without promoter or enhancer will be employed (4,5,6). Putative promoter inserts of varying sizes will be subcloned into a CAT expression vector (6,7). Internal deletion constructs will be generated by taking advantage of either internal restriction sites or by partial digestion of internal sites if these sites are not unique. These constructs will be transfected into E11-NMT cells that display high levels of PEG-3 expression. The CAT construct with minimal 5'-flanking region showing the highest degree of expression will be identified as the PEG-3 gene promoter.

The functionality of the PEG-3 promoter will be determined in E11-NMT, CREF cells treated with MMS and gamma irradiation and CREF cells transformed by the Ha-ras and v-src oncogenes. Various CAT constructs will be transfected into these cell lines by the lipofectin method or electroporation (Gene Pulser, Bio-Rad) as previously described (4,8). To correct for DNA uptake and cell number used for each transfection experiment, the CAT constructs will be cotransfected with plasmids containing bacterial β-gal gene under the control of an Rous sarcoma virus (RSV) promoter. The CAT and β-galactosidase enzymatic activities will be determined using standard protocols (4,6, 7). Minimal 5'-flanking region displaying the highest CAT activity will be identified as the promoter region for that tissue cell type or experimental condition. If no induction of CAT activity is apparent, further subcloning and screening of cosmid or phage clones would be performed until a PEG-3 promoter of sufficient length to mediate CAT induction in E11-NMT, CREF cells treated with MMS and gamma irradiation and CREF cells transformed by the Ha-ras and v-src oncogenes is obtained.

Once the promoter of PEG-3 is identified it will be subcloned into a vector adjacent to a bacterial β-gal gene, PEG-3-Prom-β-gal fusion (4). This construct will allow activation of the β-gal gene as a function of transcription from the PEG-3 promoter. The vector construct will also contain a bacterial antibiotic resistance gene, such as the neomycin or hygromycin gene, that will permit selection of cells containing the PEG-3-Prom-β-gal fusion. This vector will be transfected into E11, E11-NMT, CREF and CREF cells transformed by Ha-ras and v-src and antibiotic resistant colonies will be selected in G418 (neomycin gene) or hygromycin (hygromycin gene) as previously described (1,8,9). Antibiotic resistant colonies will be isolated and maintained as independent cell lines. Clones constitutively expressing the PEG-3-Prom-β-gal gene (E11-NMT and CREF cells transformed by the Ha-ras and v-src oncogenes) will be identified by growth in the appropriate substrate resulting in a blue color. Similarly, clones containing an inducible PEG-3-Prom-β-gal gene (E11 and CREF cells) will be identified by treating cells with MMS or gamma irradiation, incubation in the appropriate substrate and identifying clones that develop a blue color. Clones displaying the appropriate properties will be further characterized by Southern blotting (DNA organization) and Northern blotting (RNA expression). Clones with constitutive or inducible β-gal expression will then be tested for alteration in expression as a function of culture conditions (low serum, high cell density, etc.), exposure to various DNA damaging agents, incubation in agents known to specifically inhibit or enhance oncogene and progression phenotypes (such as caffeic acid phenethyl ester, phorbol ester tumor promoters, farnesyl transferase inhibitors, etc.), chemotherapeutic agents, viral infection, etc. These studies will provide useful baseline information as to the potential use of the specific constructs as biosensor monitors for agents capable of modifying cancer progression, oncogenic transformation and DNA damage and repair pathways.

Identifying cis-acting elements in the PEG-3 promoter responsible for expression in progressed cancer cells, oncogene transformed CREF cells and DNA damaged cells. Once a functional PEG-3 promoter has been identified studies will be conducted to locate cis-acting elements responsible for expression of PEG-3 in E11-NMT, oncogene transformed CREF (Ha-ras and v-src) and MMS treated CREF cells. To identify cis-acting DNA sequences, the DNA fragment displaying maximal promoter function in a transient transfection assay in E11-NMT, oncogene transformed CREF and MMS treated CREF cells will be sequenced. Potential regulatory elements will be defined by comparison to previously characterized transcriptional motifs. The importance of these sequences in regulating PEG-3 expression will be determined by introducing point mutations in a specific cis element into the promoter region using previously described site-specific mutagenesis techniques (4,9–12) or with recently described PCR-based strategies, i.e., ExSite™ PCR-based site-directed mutagenesis kit and the Chameleon™ double-stranded site-directed mutagenesis kit (Stratagene, Calif.). The mutated promoter constructs will be cloned into CAT expression vectors and tested for their effects on the promoter function by transfecting into different cell types displaying CAT activity. If increased detection sensitivity is required, the various promoter region mutants will be subcloned into a luciferase reporter construct (7).

Identifying trans-acting nuclear proteins that mediate transcriptional enhancing activity of the PEG-3 in progressed cancer cells, oncogene transformed CREF cells and in DNA damaged CREF cells. The current view on regulation of eukaryotic gene expression suggests that trans-acting proteins bind to specific sites within cis-elements of a promoter region resulting in transcriptional activation (13, 14). Experiments will be performed to identify trans-acting factors (nuclear proteins) and determine where these factors interact with cis-regulatory elements. To achieve this goal, two types of studies will be performed, one involving gel retardation (gel shift) assays (4,15–17) and the second involving DNase-I footprinting (methylation interference) assays (4).

Gel shift assays will be used to analyze the interactions between cis-acting elements in the PEG-3 promoter and trans-acting factors in mediating transcriptional control (4,15–17). To begin to identify the trans-acting factors, different non-labeled DNAs (including TATA, CAT, TRE, Sp-I binding site, NFkB, CREB, TRE, TBP, etc.) can be used as competitors in the gel shift assay to determine the relationship between the trans-acting factors and other previously identified transcriptional regulators. It is possible that the trans-acting factors regulating transcriptional control of the PEG-3 gene may be novel. To identify these factors extracts will be purified from E11-NMT cells by two cycles of heparin-Sepharose column chromatography, two cycles of DNA affinity chromatography and separation on SDS-polyacrylamide gels (18,19). Proteins displaying appropriate activity using gel shift assays will be digested in situ with trypsin, the peptides separated by HPLC and the peptides sequenced (20). Peptide sequences will be used to synthesize degenerate primers and RT-PCR will be used to identify putative genes encoding the trans-acting factor. These partial sequences will be used with cDNA library screening approaches and the RACE procedure, if necessary, to identify full-length cDNAs encoding the trans-acting factors (21–23). Once identified, the role of the trans-acting factors in eliciting PEG-3 induction following DNA damage in CREF and constitutive expression in E11-NMT, CREF-ras and CREF-src cells will be determined.

The functionality of positive and negative trans-acting factors will be determined by transiently and stably expressing these genes in E11 and E11-NMT cells to determine effects on the progression phenotype, CREF and CREF-ras and CREF-src cells to determine effects on oncogene transformation and in CREF and MMS treated CREF cells to determine the effects of DNA damage on PEG-3 induction. Positive effects would be indicated if overexpressing a positive trans-acting factor facilitates progression, expression of the oncogenic phenotype and/or a DNA-damage inducible response, whereas overexpressing a negative trans-acting factor inhibits progression, oncogene transformation and/or a DNA-damage inducible response.

Antisense approaches will be used to determine if blocking the expression of positive or negative trans-acting factors can directly modify progression, oncogenic transformation and/or DNA damage repair pathways. A direct effect of positive trans-acting factors in affecting cellular phenotype would be suggested if antisense inhibition of the positive acting factor partially or completely inhibits the progression and oncogene transformation phenotypes and/or DNA-damage and repair pathways. Conversely, a direct effect of negative trans-acting factors in inhibiting expression of PEG-3 and progression, oncogene transformation and/or DNA-damage and repair pathways would be suggested if antisense inhibition of the negative factor facilitates PEG-3 expression and the progression, oncogene transformation and/or DNA-damage inducible response pathways. Depending on the results obtained, cis-element knockouts could be used to further define the role of these elements in regulating PEG-3 expression.

For DNase-I footprinting assays, nuclear extracts from E11, E11-NMT, CREF, CREF-ras, CREF-src and MMS treated CREF cells will be prepared and DNase-I footprinting assays will be performed as described (4,6). The differential protection between nuclear extracts from E11-NMT and E11 and MMS treated CREF, CREF-ras and CREF-src cells will provide relevant information concerning the involvement of trans-acting factors in activation and the location of specific sequences in the cis-regulatory elements of the PEG-3 promoter mediating this activation. If differential protection is not detected using this approach, the sensitivity of the procedure can be improved by using different sized DNA fragments from the PEG-3 promoter region or by using partially purified nuclear extracts (4,6).

The studies briefly described above will result in the identification and cloning of the PEG-3 promoter region, the identification of cis-acting regulatory elements in the PEG-3 promoter and the identification of trans-acting regulatory elements that activate (or repress) expression of the PEG-3 gene in unprogressed and progressed cancer cells, untransformed and oncogene transformed cells and undamaged and DNA damaged cells. Experiments will also determine if cells containing a PEG-3-Prom-β-gal fusion gene can be used as a biosensor monitoring system for the progression, oncogene transformation and DNA damage and repair pathways. These reagents will be useful in defining the mechanism underlying the differential expression of PEG-3 in progressed and oncogene transformed cancer cells and during induction of DNA damage and repair. This information should prove valuable in designing approaches for selectively inhibiting PEG-3 expression, and therefore potentially modifying cancer and DNA damage resulting from treatment with physical and chemical carcinogens.

Figure 9:
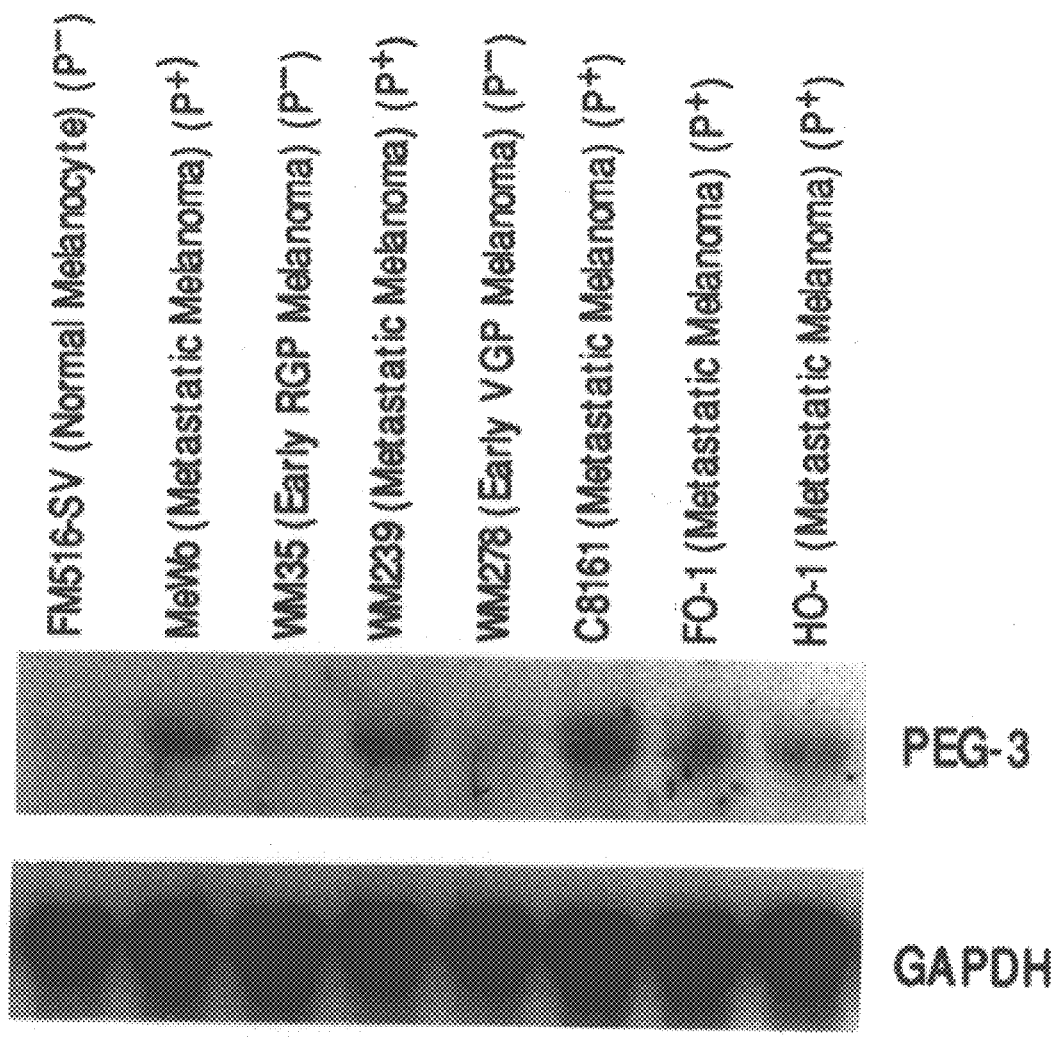
FIG. 9. PEG-3 expression in normal human melanocyte and melanoma cell lines. Fifteen µg of cellular RNA isolated from the indicated cell types, wre electrophoresed, transferred to nylon membranes and hybridized with an ~700 bp 3' region of the PEG-3 gene (top) and then stripped and probed with GAPDH (bottom). Cell types include: FM516-SV, normal human melanocyte immortalized with the SV40 T-antigen; MeWo, WM239, C8161, F0-1 and Ho-1, metastatic human melanoma; WM35, early radial growth phase (RGP) primary human melanoma; and WM278, early vertical growth phase (VGP) primary human melanoma.

2. Identifying a Human Homologue of the Rat PEG-3 Gene and Defining the Genomic Structure and the Pattern of Expression of the PEG-3 Gene Probing Northern blots containing total cytoplasmic RNA from human melanoma cells displaying different stages of cancer progression, i.e., normal melanocytes, early radial growth phase (RGP) primary human melanoma, early and late vertical growth phase (VGP) primary human melanoma and metastatic human melanoma cells, indicate that PEG-3 expression is highest in more advanced metastatic human melanoma (FIG. 9). Treatment of human melanoma cells, containing a wild-type p53 or a mutant p53 gene, with gamma irradiation results in enhanced PEG-3 expression (FIG. 10). These results suggest that a human homologue of rat PEG-3 is present in human melanoma cells and induction of this gene correlates with cancer progression and DNA damage. Human genomic clones of PEG-3 will be isolated by screening a human melanoma genomic lambda library with sequences corresponding to the carboxyl terminus of PEG-3 (that is significantly different from gadd34 and MyD116) and by PCR based genomic DNA amplification procedures (4)

The isolated positive clones will be characterized by restriction mapping, and suitable restriction fragments will be subcloned into the pBluescript vector (Strategene) (24). Exons will be identified by hybridization of the genomic fragments of a panel of PEG-3 clones and subsequent comparison of the genomic DNA sequences to that of the cDNA (25,26). A given intron/exon boundary will be indicated when the sequence from the genomic clones diverges from that of the cDNA. The size of each intron will be estimated by restriction mapping (4,25,26). An alternative approach for identifying intron/exon junctions will use a set of different restriction endonucleases to digest the human genomic DNAs. Restriction fragments resulting from this digestion will be ligated with appropriate cDNA sequences and the other specific primer to the linker sequences. By using a panel of PEG-3 cDNA oligonucleotides as primers, PCR products will be generated, that contain most, if not all, uncloned genomic DNA adjacent to PEG-3 exon sequence (25,26). The PCR products obtained will be cloned and sequenced to deduce the intron/exon boundaries of the PEG-3 gene.

Having a human genomic clone of PEG-3 will permit a direct determination of possible structural alterations and mutations in the PEG-3 gene (or its promoter) in human cancers. Tumor and normal tissue samples will be collected in pairs from patients. Genomic DNAs will be extracted from these samples (4) and analyzed by Southern blotting with appropriate restriction enzymes for possible heterozygous deletions, homozygous deletions, insertions and/or rearrangements (27,28). To detect point mutations, pairs of oligonucleotide primers for the exons will be designed for single-strand conformation polymorphism (SSCP) analysis (27,28).

The studies briefly described above will delineate the structure of the human PEG-3 gene and identify structural changes in the PEG-3 gene (or its promoter) in cancer versus normal tissue. A high frequency of structural alterations and mutations, especially those that can potentially alter the expression and functionality of the PEG-3 protein, in normal versus cancer tissue or in early versus late stage cancers, would suggest that these alterations in the PEG-3 gene may be involved in initiation and/or progression of this cancer. Additionally, experiments to determine the state of methylation of the PEG-3 promoter region should prove informative (29).

If specific mutations in PEG-3 (or its promoter) are found to correlate with cancer development and/or evolution, the effect of such mutations on the in vitro and in vivo biological properties of cells can be determined. Mutations will be introduced that alter the normal PEG-3 gene to generate a progression specific PEG-3 gene product. To achieve these goals, the PEG-3 gene will be mutagenized at specific sites, using the ExSite™ PCR-based site-directed mutagenesis kit and the Chameleon™ double-stranded site-directed mutagenesis kit (Stratagene, La Jolla, Calif.). We have documented experience in introducing mutations in defined regions of the adenovirus genome and characterizing these genetic changes (9–12). Once identified and characterized, mutant constructs of the PEG-3 gene will be transfected into appropriate target cells to determine the effects of specific mutations in PEG-3 on cellular phenotype.

SECOND SERIES OF REFERENCES

1. Su Z-z, Shi Y & Fisher P B (1994) *Proc Natl Acad Sci USA*, in submission.
2. Siebert P, Chen S & Kellogg D (1995) *CLONTECHniques*, X (2)L: 1–3.
3. Siebert P, Chenchik A, Kellogg D E, Lukyanov K A & Lukyanov S A (1995) *Nucleic Acids Res*, 23: 1087–1088.
4. Sambrook J, Fritsch E F & Maniatis T. In: *Molecular Cloning: A Laboratory Manual*, 2nd edition, Cold Spring Harbor Laboratories Press, Cold Spring Harbor, N.Y., 1989.
5. Duigou G J, Su Z-z, Babiss L E, Driscoll B, Fung Y-K T & Fisher P B. (1991) *Oncogene* 6:1813–1824.
6. Shen R, Goswami S K, Mascareno E, Kumar A & Siddiqui MAQ. (1991) *Mol Cell Biol* 11: 1676–1685.
7. Fisher A L, Ohsako S & Caudy M. (1996) *Mol Cell Biol* 16:2670–2677.
8. Jiang H, Lin J J, Su Z-z, Goldstein N I & Fisher P B (1995) *Oncogene* 11:2477–2486.
9. Babiss L E, Fisher P B & Ginsberg H S. (1984) *J Virol* 49:731–740.
10. Babiss L E, Fisher P B & Ginsberg H S. (1984) *J Virol* 52:389–395.
11. Herbst R S, Hermo H Jr, Fisher P B & Babiss L E. (1988) *J Virol* 62:4634–4643.
12. Su Z-z, Shen R, Young C S H & Fisher P B. (1993) *Mol Carcinog* 8:155–166.
13. Maniatis T, Goodbourn S & Fischer A. (1987) *Science* 236:1237–1244.
14. Ptashne M. (1988) *Nature* 335:683–689.
15. Su Z-z, Yemul S, Stein C A & Fisher P B. (1995) *Oncogene* 10:2037–2049.
16. Jiang H, Lin J, Young S-m, Goldstein N I, Waxman S, Davila V, Chellappan S P & Fisher P B. (1995) *Oncogene* 11:1179–1189.
17. Su Z-z, Shen R, O'Brian C A & Fisher P B. (1994) *Oncogene* 9:1123–1132.
18. Kamat J P, Basu K, Satyamoorthy L, Showe L & Howe C C (1995) *Mol Rep Dev* 41:8–15.
19. Basu A, Dong B, Krainer A R & Howe C C (1997) *Mol Cell Biol* 17:677–686.
20. Aebersold R H, Leavitt R A, Saavedra R A, Hood L E & Kent S B H (1987) *Proc Natl Acad Sci USA* 84:6970–6974.
21. Jiang H, Lin J, Su Z-z, Kerbel R S, Herlyn M, Weissman R B, Welch D R & Fisher P B. (1995) *Oncogene* 10:1855–1864.
22. Jiang H, Lin J J, Su Z-z, Goldstein N I & Fisher P B (1995) *Oncogene* 11:2477–2486.
23. Lin J J, Jiang H & Fisher P B (1996) *Mol Cell Different* 4:317–333.
24. Reddy P G, Su Z-z & Fisher P B Methods in Molecular Genetics, vol. 1, K W Adolph, Ed, Academic Press, Inc, Orlando, Fla., pp 68–102, 1993.
25. Hong F D, Huang H-S, To H, Young L-J H S, Oro A, Bookstein R, Lee E Y-H P & Lee W H (1989) *Proc Natl Acad Sci USA* 86:5502–5506.
26. Sun J, Rose J B & Bird P (1995) *J Biol Chem* 270:16089–16096.
27. Puffenberger E G, Hosoda K, Washington S S, Nakao K, deWit D, Yanagisawa M and Charkravarti A. (1994) *Cell* 79:1257–1266.

28. Washimi O, Nagatake M, Osada H, Ueda R, Koshikawa T, Seki T, Takahashi T and Takahashi T (1995) *Cancer Res* 55:514–517.
29. Babiss L E, Zimmer S G & Fisher P B (1985) *Science* 228:1099–1101.

Third Series of Experiments

Expression of PEG-3 in human melanoma cells

Studies were also performed to evaluate PEG-3 expression in human melanoma cells and to determine whether induction or increased expression occurs during DNA damage. PEG-3 is expressed de novo in advanced stage tumorigenic and metastatic human melanoma cell lines (MeWo, WM239, C8161, F0-1 and H0-1), whereas expression is reduced in immortalized normal human melanocyte (FM516-SV) and RGP (WM35) and early VGP (WM278) primary melanomas (FIG. 9). Moreover, PEG-3 expression is enhanced following exposure to gamma irradiation, but is not elevated following a similar dose of MMS (100 mg/ml) inducing PEG-3 expression in CREF cells (FIG. 10). Using a p53 mutant and p53 wild-type human melanoma cell lines, it is apparent that PEG-3 induction by gamma irradiation in human melanoma can occur by a wild-type p53 independent pathway (FIG. 10). These results indicate that the PEG-3 response is not restricted to rodent cells treated with specific DNA damaging agents, but insteiad is a more general response in mammalian cells. Furthermore, there appears to be a direct relationship between PEG-3 expression and human melanoma progression.

Clarifying the role of PEG-3 in human cancer progression

To define the role of the PEG-3 gene in human cancer progression it will be essential to obtain a human homologue of this gene. This will be achieved by low stringency hybridization screening of a human melanoma cDNA library (1) and by PCR-based approaches using primers designed from the rat PEG-3 sequences that are highly homologous with gadd34 and MyD116 (4,5). Once a full-length PEG-3 (Hu) cDNA is obtained it will be sequenced and in vitro translated to insure production of the appropriate sized protein (3–5). This gene can then be used to define patterns of expression, by Northern blotting analysis, in normal, benign and metastatic human tumor cell lines and primary patient-derived samples (2–5). This survey will indicate the level of coordinate expression between PEG-3 and human cancer progression. Clearly, if PEG-3 is shown to be a regulator of the progression phenotype in human malignancies, a large number of interesting and important experiments could be conducted to amplify on this observation. However, these studies would not be in the current scope of this grant because of limited personnel and resources. The types of studies that could and should be conducted include: (a) production of monoclonal antibodies interacting with PEG-3 (Hu) and evaluation of these reagents for cancer diagnostic purposes; (b) cellular localization studies with PEG-3 (Hu) monoclonal antibodies to define potential targets for activity; (c) mapping the chromosomal location of PEG-3 (Hu) in the genome to determine any association between previously identified regions associated with cancer; (d) identification and characterization of the genomic structure of PEG-3 (Hu) and determining if alterations in structure correlate with cancer progression; (e) determine by nuclear run-on and mRNA degradation assays if PEG-3 (Hu) expression is controlled at a transcriptional or postranscriptional level; (f) identification and characterization, if PEG-3 expression is regulated transcriptionally, of the promoter region of PEG-3 (Hu) to define the mechanism of regulation of this gene in progressed cancer cells; (g) the identification and characterization of cis-acting elements and trans-regulating factors (nuclear proteins) regulating PEG-3 (Hu) expression; (h) defining the role of PEG-3 expression in vivo by creating knockout mice and tissue specific knockout mice; and (i) determining, using transgenic mice and the tyrosinase promoter, the role of overexpression of PEG-3 in normal melanocyte development. These studies would provide important information about a potentially exciting and novel gene with direct relevance to human cancer progression.

THIRD SERIES OF REFERENCES

1. Jiang, H. and P. Fisher Use of a sensitive and efficient subtraction hybridization protocol for the identification of genes differentially regulated during the induction of differentiation in human melanoma cells. Mol Cell Different. 1: 285–299, 1993.
2. Jiang, H., et al. The melanoma differentiation associated gene mda-6, which encodes the cyclin-dependent kinase inhibitor p21 is differentially expressed during growth, differentiation and progression in human melanoma cells. Oncogene 10:1855–1864, 1995.
3. Jiang, H., et al. Subtraction hybridization identifies a novel melanoma differentiation associated gene, mda-7, modulated during human melanoma differentiation, growth and progression. Oncogene, 11: 2477–2486, 1995.
4. Shen, R., et al. Identification of the human prostatic carcinoma oncogene PTI-1 by rapid expression cloning and differential RNA display. PNAS, USA 92: 6778–6782, 1995.
5. Su, Z-Z, et al. Surface-epitope masking and expression cloning identifies the human prostate carcinoma tumor antigen gene PCTA-1 a member of the galectin gene family. PNAS, USA, 93:7252–7257, 1996.

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 457 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

```
Met Ala Pro Ser Pro Arg Pro Gln His Val Leu His Trp Lys Glu Ala
1               5                   10                  15

His Ser Phe Tyr Leu Leu Ser Pro Leu Met Gly Phe Leu Ser Arg Ala
            20                  25                  30

Trp Ser Arg Leu Arg Gly Pro Glu Val Ser Glu Ala Trp Leu Ala Glu
        35                  40                  45

Thr Val Ala Gly Ala Asn Gln Ile Glu Ala Asp Ala Leu Leu Thr Pro
    50                  55                  60

Pro Pro Val Ser Glu Asn His Leu Pro Leu Arg Glu Thr Glu Gly Asn
65                  70                  75                  80

Gly Thr Pro Glu Trp Ser Lys Ala Ala Gln Arg Leu Cys Leu Asp Val
                85                  90                  95

Glu Ala Gln Ser Ser Pro Pro Lys Thr Trp Gly Leu Ser Asp Ile Asp
            100                 105                 110

Glu His Asn Gly Lys Pro Gly Gln Asp Gly Leu Arg Glu Gln Glu Val
        115                 120                 125

Glu His Thr Ala Gly Leu Pro Thr Leu Gln Pro Leu His Leu Gln Gly
    130                 135                 140

Ala Asp Lys Lys Val Gly Glu Val Val Ala Arg Glu Glu Gly Val Ser
145                 150                 155                 160

Glu Leu Ala Tyr Pro Thr Ser His Trp Glu Gly Pro Ala Glu Asp
                165                 170                 175

Glu Glu Asp Thr Glu Thr Val Lys Lys Ala His Gln Ala Ser Ala Ala
            180                 185                 190

Ser Ile Ala Pro Gly Tyr Lys Pro Ser Thr Ser Val Tyr Cys Pro Gly
        195                 200                 205

Glu Ala Glu His Arg Ala Thr Glu Glu Lys Gly Thr Asp Asn Lys Ala
    210                 215                 220

Glu Pro Ser Gly Ser His Ser Arg Val Trp Glu Tyr His Thr Arg Glu
225                 230                 235                 240

Arg Pro Lys Gln Glu Gly Glu Thr Lys Pro Glu Gln His Arg Ala Gly
                245                 250                 255

Gln Ser His Pro Cys Gln Asn Ala Glu Ala Glu Glu Gly Gly Pro Glu
            260                 265                 270

Thr Ser Val Cys Ser Gly Ser Ala Phe Leu Lys Ala Trp Val Tyr Arg
        275                 280                 285

Pro Gly Glu Asp Thr Glu Glu Glu Asp Ser Asp Leu Asp Ser Ala
    290                 295                 300

Glu Glu Asp Thr Ala His Thr Cys Thr Thr Pro His Thr Ser Ala Phe
305                 310                 315                 320

Leu Lys Ala Trp Val Tyr Arg Pro Gly Glu Asp Thr Glu Glu Glu Asp
                325                 330                 335

Asp Gly Asp Trp Asp Ser Ala Glu Glu Asp Ala Ser Gln Ser Cys Thr
            340                 345                 350

Thr Pro His Thr Ser Ala Phe Leu Lys Ala Trp Val Tyr Arg Pro Gly
        355                 360                 365

Glu Asp Thr Glu Glu Glu Asp Asp Ser Glu Asn Val Ala Pro Val Asp
    370                 375                 380

Ser Glu Thr Val Asp Ser Cys Gln Ser Thr Gln His Cys Leu Pro Val
385                 390                 395                 400
```

-continued

```
Glu Lys Thr Lys Gly Cys Gly Glu Ala Glu Pro Pro Phe Gln Trp
                405                 410                 415

Pro Ser Ile Tyr Leu Asp Arg Ser Gln His His Leu Gly Leu Pro Leu
            420                 425                 430

Ser Cys Pro Phe Asp Cys Arg Ser Gly Ser Asp Leu Ser Lys Pro Pro
            435                 440                 445

Pro Gly Ile Arg Ala Leu Arg Phe Leu
450                 455
```

(2) INFORMATION FOR SEQ ID NO:2:

(i) SEQUENCE CHARACTERISTICS:
        (A) LENGTH: 590 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Ala Pro Ser Pro Arg Pro Gln His Ile Leu Leu Trp Arg Asp Ala
1               5                   10                  15

His Ser Phe His Leu Leu Ser Pro Leu Met Gly Phe Leu Ser Arg Ala
                20                  25                  30

Trp Ser Arg Leu Arg Val Pro Glu Ala Pro Glu Pro Trp Pro Ala Glu
            35                  40                  45

Thr Val Thr Gly Ala Asp Gln Ile Glu Ala Asp Ala His Pro Ala Pro
        50                  55                  60

Pro Leu Val Pro Glu Asn His Pro Pro Gln Gly Glu Ala Glu Glu Ser
65                  70                  75                  80

Gly Thr Pro Glu Glu Gly Lys Ala Ala Gln Gly Pro Cys Leu Asp Val
                85                  90                  95

Gln Ala Asn Ser Ser Pro Pro Glu Thr Leu Gly Leu Ser Asp Asp Asp
                100                 105                 110

Lys Gln Gly Gln Asp Gly Pro Arg Glu Gln Gly Arg Ala His Thr Ala
            115                 120                 125

Gly Leu Pro Ile Leu Leu Ser Pro Gly Leu Gln Ser Ala Asp Lys Ser
        130                 135                 140

Leu Gly Glu Val Val Ala Gly Glu Gly Val Thr Glu Leu Ala Tyr
145                 150                 155                 160

Pro Thr Ser His Trp Glu Gly Cys Pro Ser Glu Glu Glu Asp Gly
                165                 170                 175

Glu Thr Val Lys Lys Ala Phe Arg Ala Ser Ala Asp Ser Pro Gly His
            180                 185                 190

Lys Ser Ser Thr Ser Val Tyr Cys Pro Gly Glu Ala Glu His Gln Ala
        195                 200                 205

Thr Glu Glu Lys Gln Thr Glu Asn Lys Ala Asp Pro Pro Ser Ser Pro
210                 215                 220

Ser Gly Ser His Ser Arg Ala Trp Glu Tyr Cys Ser Lys Gln Glu Gly
225                 230                 235                 240

Glu Ala Asp Pro Glu Pro His Arg Ala Gly Lys Tyr Gln Leu Cys Gln
                245                 250                 255

Asn Ala Glu Ala Glu Glu Glu Glu Ala Lys Val Ser Ser Leu Ser
                260                 265                 270

Val Ser Ser Gly Asn Ala Phe Leu Lys Ala Trp Val Tyr Arg Pro Gly
        275                 280                 285
```

```
Glu Asp Thr Glu Asp Asp Asp Ser Asp Trp Gly Ser Ala Glu Glu
    290                 295                 300

Glu Gly Lys Ala Leu Ser Ser Pro Thr Ser Pro Glu His Asp Phe Leu
305                 310                 315                 320

Lys Ala Trp Val Tyr Arg Pro Gly Glu Asp Thr Glu Asp Asp Asp
                325                 330                 335

Ser Asp Trp Gly Ser Ala Glu Glu Gly Lys Ala Leu Ser Ser Pro
            340                 345                 350

Thr Ser Pro Glu His Asp Phe Leu Lys Ala Trp Val Tyr Arg Pro Gly
    355                 360                 365

Glu Asp Thr Glu Asp Asp Gln Asp Ser Asp Trp Gly Ser Ala Glu Lys
    370                 375                 380

Asp Gly Leu Ala Gln Thr Phe Ala Thr Pro His Thr Ser Ala Phe Leu
385                 390                 395                 400

Lys Thr Trp Val Cys Cys Pro Gly Glu Asp Thr Glu Asp Asp Asp Cys
                405                 410                 415

Glu Val Val Val Pro Glu Asp Ser Glu Ala Ala Asp Pro Asp Lys Ser
                420                 425                 430

Pro Ser His Glu Ala Gln Gly Cys Leu Pro Gly Glu Gln Thr Glu Gly
            435                 440                 445

Leu Val Glu Ala Glu His Ser Leu Phe Gln Val Ala Phe Tyr Leu Pro
    450                 455                 460

Gly Glu Lys Pro Ala Pro Pro Trp Thr Ala Pro Lys Leu Pro Leu Arg
465                 470                 475                 480

Leu Gln Arg Arg Leu Thr Leu Leu Arg Thr Pro Thr Gln Asp Gln Asp
                485                 490                 495

Pro Glu Thr Pro Leu Arg Ala Arg Lys Val His Phe Ser Glu Asn Val
            500                 505                 510

Thr Val His Phe Leu Ala Val Trp Ala Gly Pro Ala Gln Ala Ala Arg
    515                 520                 525

Arg Gly Pro Trp Glu Gln Leu Ala Arg Asp Arg Ser Arg Phe Ala Arg
    530                 535                 540

Arg Ile Ala Gln Ala Glu Glu Lys Leu Gly Pro Tyr Leu Thr Pro Ala
545                 550                 555                 560

Phe Arg Ala Arg Ala Trp Ala Arg Leu Gly Asn Pro Ser Leu Pro Leu
                565                 570                 575

Ala Leu Glu Pro Ile Cys Asp His Thr Phe Phe Pro Ser Gln
            580                 585                 590

(2) INFORMATION FOR SEQ ID NO:3:

(i) SEQUENCE CHARACTERISTICS:
        (A) LENGTH: 657 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Met Ala Pro Ser Pro Arg Phe Gln His Val Leu His Trp Arg Asp Ala
1               5                   10                  15

His Asn Phe Tyr Leu Leu Ser Pro Leu Met Gly Leu Leu Ser Arg Ala
                20                  25                  30

Trp Ser Arg Leu Arg Gly Pro Glu Val Pro Glu Ala Trp Leu Ala Lys
                35                  40                  45
```

```
Thr Val Thr Gly Ala Asp Gln Ile Glu Ala Ala Ala Leu Leu Thr Pro
    50                  55                  60

Thr Pro Val Ser Gly Asn Leu Leu Pro His Gly Glu Thr Glu Ser
65              70                  75                  80

Gly Ser Pro Glu Gln Ser Gln Ala Ala Gln Arg Leu Cys Leu Val Glu
                85                  90                  95

Ala Glu Ser Ser Pro Pro Glu Thr Trp Gly Leu Ser Asn Val Asp Glu
            100                 105                 110

Tyr Asn Ala Lys Pro Gly Gln Asp Asp Leu Arg Glu Lys Glu Met Glu
            115                 120                 125

Arg Thr Ala Gly Lys Ala Thr Leu Gln Pro Ala Gly Leu Gln Gly Ala
        130                 135                 140

Asp Lys Arg Leu Gly Glu Val Val Ala Arg Glu Gly Val Ala Glu
145                 150                 155                 160

Pro Ala Tyr Pro Thr Ser Gln Leu Glu Gly Gly Pro Ala Glu Asn Glu
                165                 170                 175

Glu Asp Gly Glu Thr Val Lys Thr Tyr Gln Ala Ser Ala Ala Ser Ile
            180                 185                 190

Ala Pro Gly Tyr Lys Pro Ser Thr Pro Val Pro Phe Leu Gly Glu Ala
        195                 200                 205

Glu His Gln Ala Thr Glu Glu Lys Gly Thr Glu Asn Lys Ala Asp Pro
    210                 215                 220

Ser Asn Ser Pro Ser Ser Gly Ser His Ser Arg Ala Trp Glu Tyr Tyr
225                 230                 235                 240

Ser Arg Glu Lys Pro Lys Gln Glu Gly Glu Ala Lys Val Glu Ala His
                245                 250                 255

Arg Ala Gly Gln Gly His Pro Cys Arg Asn Ala Glu Ala Glu Glu Gly
                260                 265                 270

Gly Pro Glu Thr Thr Phe Val Cys Thr Gly Asn Ala Phe Leu Lys Ala
            275                 280                 285

Trp Val Tyr Arg Pro Gly Glu Asp Thr Glu Glu Asp Asn Ser Asp
    290                 295                 300

Ser Asp Ser Ala Glu Glu Asp Thr Ala Gln Thr Gly Ala Thr Pro His
305                 310                 315                 320

Thr Ser Ala Phe Leu Lys Ala Trp Val Tyr Arg Pro Gly Glu Asp Thr
                325                 330                 335

Glu Glu Glu Asp Ser Asp Ser Asp Ser Ala Glu Glu Asp Thr Ala Gln
            340                 345                 350

Thr Gly Ala Thr Pro His Thr Ser Ala Phe Leu Lys Ala Trp Val Tyr
        355                 360                 365

Arg Pro Gly Glu Asp Thr Glu Glu Glu Asn Ser Asp Leu Asp Ser Ala
    370                 375                 380

Glu Glu Asp Thr Ala Gln Thr Gly Ala Thr Pro His Thr Ser Ala Phe
385                 390                 395                 400

Leu Lys Ala Trp Val Tyr Arg Pro Gly Glu Asp Thr Glu Glu Asn
                405                 410                 415

Ser Asp Leu Asp Ser Ala Glu Glu Asp Thr Ala Gln Thr Gly Ala Thr
            420                 425                 430

Pro His Thr Ser Pro Phe Leu Lys Ala Trp Val Tyr Arg Pro Gly Glu
        435                 440                 445

Asp Thr Glu Asp Thr Glu Glu Glu Asp Ser Glu Asn Val Ala
    450                 455                 460
```

Pro Gly Asp Ser Glu Thr Ala Asp Ser Ser Gln Ser Pro Cys Leu Gln
465                 470                 475                 480

Pro Gln Arg Cys Leu Pro Gly Glu Lys Thr Lys Gly Arg Gly Glu Glu
            485                 490                 495

Pro Pro Leu Phe Gln Val Ala Phe Tyr Leu Pro Gly Glu Lys Pro Glu
        500                 505                 510

Ser Pro Trp Ala Ala Pro Lys Leu Pro Leu Arg Leu Gln Arg Arg Leu
    515                 520                 525

Arg Leu Phe Lys Ala Pro Thr Arg Asp Gln Asp Pro Glu Ile Pro Leu
530                 535                 540

Lys Ala Arg Lys Val His Phe Ala Glu Lys Val Thr Val His Phe Leu
545                 550                 555                 560

Ala Val Trp Ala Gly Pro Ala Gln Ala Ala Arg Arg Gly Pro Trp Glu
                565                 570                 575

Gln Phe Ala Arg Asp Arg Ser Arg Phe Ala Arg Arg Ile Ala Gln Ala
            580                 585                 590

Glu Glu Lys Leu Gly Pro Tyr Leu Thr Pro Asp Ser Arg Ala Arg Ala
        595                 600                 605

Trp Ala Arg Leu Arg Asn Pro Ser Leu Pro Gln Ser Glu Pro Arg Ser
    610                 615                 620

Ser Ser Glu Ala Thr Pro Leu Thr Gln Asp Val Thr Thr Pro Ser Pro
625                 630                 635                 640

Leu Pro Ser Glu Thr Pro Ser Pro Ser Leu Tyr Leu Gly Gly Arg Arg
                645                 650                 655
Gly (2) INFORMATION FOR SEQ ID NO:4:

(i) SEQUENCE CHARACTERISTICS:
        (A) LENGTH: 2137 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
CTGCAGTACT TGTACATTGC TAAATAAAGA GAGGGACTCC AGGAGGAGCA GCCTGGGTCT      60

AAGAGGTAGG CAGAAGGAGG TTTTAGGGGC CTGAGCACAA GCTTGAGGAG AGAAAGGTTA     120

TTAAAAAGCC AGACGCTTAC AGGTCTCAGA AGGGCTAGCC AGAAACTGTG GCTGGGGTTA     180

AGGAAAGGGT TTAAGAGTGT GGGCTTTTGG TTCTGAGGAT GTAGAACGTG AATGTTGAGA     240

GAAGAACCAA GTGGCGGAGT TGGGTGTGAG CAATGCTATT AGGAATTTGA GGCAGGGATT     300

CACGCGCTGC TGTGACTATT TTTTAACAAT GACTCAGTGC TGTGACCTGA TACTGTTTCC     360

AGAGCGACTT CTAAACAAAT TCCCCCTTTC TAGGCCAGAC ACATGGCCCC AAGCCCAAGA     420

CCCCAGCATG TCCTGCACTG GAAGGAAGCC CACTCTTTCT ACCTCCTGTC TCCACTGATG     480

GGCTTCCTCA GCCGGGCCTG GAGCCGCCTG AGGGGGCCCG AGGTCTCAGA GGCCTGGTTG     540

GCAGAAACAG TAGCAGGAGC AAACCAGATA GAGGCTGATG CTCTGTTGAC GCCTCCCCCG     600

GTCTCTGAAA ATCACCTACC TCTCCGAGAG ACTGAAGGAA ATGGAACTCC TGAATGGAGT     660

AAAGCAGCCC AGAGGCTCTG CCTTGATGTG GAAGCCCAAA GTTCCCCTCC TAAAACTTGG     720

GGACTTTCAG ATATTGATGA ACATAATGGG AAGCCAGGAC AAGATGGCCT TAGAGAGCAA     780

GAAGTGGAGC ACACAGCTGG CCTGCCTACA CTACAGCCCC TTCACCTGCA AGGGGCAGAT     840
```

-continued

```
AAGAAAGTTG GGGAGGTGGT GGCTAGAGAA GAGGGTGTGT CCGAGCTGGC TTACCCCACA      900

TCACACTGGG AGGGTGGTCC AGCTGAGGAT GAAGAGGATA CAGAAACCGT GAAGAAGGCT      960

CACCAGGCCT CTGCTGCTTC CATAGCTCCA GGATATAAAC CCAGCACTTC TGTGTATTGC     1020

CCAGGGGAGG CAGAACATCG AGCCACGGAG GAAAAAGGAA CAGACAATAA GGCTGAACCC     1080

TCAGGCTCCC ACTCCAGAGT CTGGGAGTAC CACACTAGAG AGAGGCCTAA GCAGGAGGGA     1140

GAAACTAAGC CAGAGCAACA CAGGGCAGGG CAGAGTCACC CTTGTCAGAA TGCAGAGGCT     1200

GAGGAAGGAG GACCTGAGAC TTCTGTCTGT TCTGGCAGTG CCTTCCTGAA GGCCTGGGTG     1260

TATCGCCCAG GAGAGGACAC AGAGGAGGAA GAAGACAGTG ATTTGGATTC AGCTGAGGAA     1320

GACACAGCTC ATACCTGTAC CACCCCCCAT ACAAGTGCCT TCCTGAAGGC CTGGGTCTAT     1380

CGCCCAGGAG AGGACACAGA AGAGGAAGAT GACGGTGATT GGGATTCAGC TGAGGAAGAC     1440

GCGTCTCAGA GCTGTACCAC CCCCCATACA AGTGCCTTCC TGAAGGCCTG GGTCTATCGC     1500

CCAGGAGAGG ACACAGAAGA GGAAGACGAC AGTGAGAATG TGGCCCCAGT TGACTCAGAA     1560

ACAGTTGACT CTTGCCAGAG TACCCAGCAT TGTCTACCAG TAGAGAAGAC CAAGGGATGT     1620

GGAGAAGCAG AGCCCCCTCC CTTCCAGTGG CCTTCTATTT ACCTGGACAG AAGCCAGCAC     1680

CACCTTGGGC TGCCCCTAAG CTGCCCCTTC GACTGCAGAA GCGGCTCAGA TCTTTCAAAG     1740

CCCCCGCCCG GAATCAGGGC CCTGAGATTC CTCTGAAGGG TAGAAAGGTG CACTTCTCTG     1800

AGAAAGTTAC AGTCCATTTC CTTGCTGTCT GGGCAGGACC AGCCCAGGCT GCTCGTCGAG     1860

GCCCCTGGGA GCAGTTTGCA CGAGATCGAA GCCGCTTTGC TCGACGCATT GCCGTCCTCG     1920

TCTCTTCCAC TGCCTGAGCC TTGCTCTTCC ACTGAGGCCA CACCCCTCAG CCAAGATGTG     1980

ACCACTCCCT CTCCCCTTCC CAGTGAAATC CCTCCTCCCA GCCTGGACTT GGGAGGAAGG     2040

CGGGCTAAGC CTGAGTAGTT TTTTGTGTAT TCTATGAGTG TTAGTCTCTT AATACGAATA     2100

TGTAACGCCT TTTGCATTTG TAAAAAAAAA AAAAAAA                              2137
```

(2) INFORMATION FOR SEQ ID NO:5:

(i) SEQUENCE CHARACTERISTICS:
        (A) LENGTH: 457 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Met Ala Pro Ser Pro Arg Pro Gln His Val Leu His Trp Lys Glu Ala
1               5                   10                  15

His Ser Phe Tyr Leu Leu Ser Pro Leu Met Gly Phe Leu Ser Arg Ala
            20                  25                  30

Trp Ser Arg Leu Arg Gly Pro Glu Val Ser Glu Ala Trp Leu Ala Glu
        35                  40                  45

Thr Val Ala Gly Ala Asn Gln Ile Glu Ala Asp Ala Leu Leu Thr Pro
    50                  55                  60

Pro Pro Val Ser Glu Asn His Leu Pro Leu Arg Glu Thr Glu Gly Asn
65                  70                  75                  80

Gly Thr Pro Glu Trp Ser Lys Ala Ala Gln Arg Leu Cys Leu Asp Val
                85                  90                  95

Glu Ala Gln Ser Ser Pro Pro Lys Thr Trp Gly Leu Ser Asp Ile Asp
            100                 105                 110

Glu His Asn Gly Lys Pro Gly Gln Asp Gly Leu Arg Glu Gln Glu Val
```

-continued

```
                115                 120                 125
Glu His Thr Ala Gly Leu Pro Thr Leu Gln Pro Leu His Leu Gln Gly
        130                 135                 140

Ala Asp Lys Lys Val Gly Glu Val Val Ala Arg Glu Glu Gly Val Ser
145                 150                 155                 160

Glu Leu Ala Tyr Pro Thr Ser His Trp Glu Gly Gly Pro Ala Glu Asp
                165                 170                 175

Glu Glu Asp Thr Glu Thr Val Lys Lys Ala His Gln Ala Ser Ala Ala
                180                 185                 190

Ser Ile Ala Pro Gly Tyr Lys Pro Ser Thr Ser Val Tyr Cys Pro Gly
        195                 200                 205

Glu Ala Glu His Arg Ala Thr Glu Glu Lys Gly Thr Asp Asn Lys Ala
        210                 215                 220

Glu Pro Ser Gly Ser His Ser Arg Val Trp Glu Tyr His Thr Arg Glu
225                 230                 235                 240

Arg Pro Lys Gln Glu Gly Glu Thr Lys Pro Glu Gln His Arg Ala Gly
                245                 250                 255

Gln Ser His Pro Cys Gln Asn Ala Glu Ala Glu Glu Gly Gly Pro Glu
                260                 265                 270

Thr Ser Val Cys Ser Gly Ser Ala Phe Leu Lys Ala Trp Val Tyr Arg
        275                 280                 285

Pro Gly Glu Asp Thr Glu Glu Glu Asp Ser Asp Leu Asp Ser Ala
        290                 295                 300

Glu Glu Asp Thr Ala His Thr Cys Thr Thr Pro His Thr Ser Ala Phe
305                 310                 315                 320

Leu Lys Ala Trp Val Tyr Arg Pro Gly Glu Asp Thr Glu Glu Glu Asp
                325                 330                 335

Asp Gly Asp Trp Asp Ser Ala Glu Glu Asp Ala Ser Gln Ser Cys Thr
                340                 345                 350

Thr Pro His Thr Ser Ala Phe Leu Lys Ala Trp Val Tyr Arg Pro Gly
                355                 360                 365

Glu Asp Thr Glu Glu Glu Asp Asp Ser Glu Asn Val Ala Pro Val Asp
        370                 375                 380

Ser Glu Thr Val Asp Ser Cys Gln Ser Thr Gln His Cys Leu Pro Val
385                 390                 395                 400

Glu Lys Thr Lys Gly Cys Gly Glu Ala Glu Pro Pro Phe Gln Trp
                405                 410                 415

Pro Ser Ile Tyr Leu Asp Arg Ser Gln His His Leu Gly Leu Pro Leu
                420                 425                 430

Ser Cys Pro Phe Asp Cys Arg Ser Gly Ser Asp Leu Ser Lys Pro Pro
        435                 440                 445

Pro Gly Ile Arg Ala Leu Arg Phe Leu
        450                 455
```

What is claimed is:

1. An isolated nucleic acid molecule encoding a rat Progression Elevated Gene-3 protein (SEQ. ID. NO. 4).

2. The isolated nucleic acid of claim 1 which is DNA.

3. The isolated nucleic acid of claim 2 which is cDNA or genomic DNA.

4. The isolated nucleic acid of claim 1 which is RNA.

5. The isolated nucleic acid molecule of claim 1 operatively linked to a regulatory element.

6. A nucleic acid comprising a unique sequence of the rat Progression Elevated Gene-3 (SEQ. ID. NO. 4).

7. A vector which comprises the isolated nucleic acid molecule of claim 1 or 6.

8. The vector of claim 7 which is a plasmid.

9. The plasmid of claim 8 designated pPEG-3 (ATCC Accession No. 97911).

10. A host vector system for the production of a polypeptide having the biological activity of a Progression Elevated Gene-3 protein which comprises the vector of claim 7 and a suitable host.

11. The host vector system of claim 10, wherein the suitable host is a bacterial cell, yeast cell, insect cell, or animal cell.

12. A method of producing a Progression Elevated Gene-3 protein which comprises growing the host vector system of claim 10 under conditions permitting production of the protein and recovering the protein so produced.

13. A method of transforming cells which comprises transfecting a host cell with a suitable vector of claim 7.

14. Transformed cells produced by the method of claims 13.

15. A composition for reversing the progression state of cells comprising an amount of the nucleic acid molecule of claim 6 effective to inhibit the expression of Progression Elevated Gene-3 and a carrier.

* * * * *